(12) United States Patent
Sowden et al.

(10) Patent No.: US 11,576,867 B2
(45) Date of Patent: Feb. 14, 2023

(54) TABLETS HAVING DISCONTINUOUS COATED REGIONS

(71) Applicant: Johnson & Johnson Consumer Inc., Skillman, NJ (US)

(72) Inventors: Harry Sowden, Glenside, PA (US); Gerard McNally, Berwyn, PA (US); Der-Yang Lee, Flemington, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 148 days.

(21) Appl. No.: 16/774,153

(22) Filed: Jan. 28, 2020

(65) Prior Publication Data

US 2020/0155463 A1    May 21, 2020

Related U.S. Application Data

(62) Division of application No. 15/652,315, filed on Jul. 18, 2017, now Pat. No. 10,583,089.

(60) Provisional application No. 62/364,059, filed on Jul. 19, 2016.

(51) Int. Cl.
| | |
|---|---|
| *A61K 9/20* | (2006.01) |
| *A61K 9/28* | (2006.01) |
| *A61K 9/00* | (2006.01) |
| *B05C 1/02* | (2006.01) |
| *B05D 1/28* | (2006.01) |
| *B05D 1/40* | (2006.01) |
| *B05C 13/02* | (2006.01) |
| *B05D 5/06* | (2006.01) |

(Continued)

(52) U.S. Cl.
CPC .......... *A61K 9/2072* (2013.01); *A61K 9/0053* (2013.01); *A61K 9/288* (2013.01); *A61K 9/2866* (2013.01); *A61K 9/2873* (2013.01); *A61K 9/2893* (2013.01); *B05C 1/027* (2013.01); *B05C 13/02* (2013.01); *B05D 1/28* (2013.01); *B05D 1/40* (2013.01); *B05D 5/06* (2013.01); *B05C 1/003* (2013.01); *B05D 1/265* (2013.01); *B05D 2258/02* (2013.01)

(58) Field of Classification Search
None
See application file for complete search history.

(56) References Cited

U.S. PATENT DOCUMENTS

| | | | |
|---|---|---|---|
| 4,279,926 A | 7/1981 | Bruzzese et al. | |
| 4,543,370 A | 9/1985 | Porter et al. | |
| 4,643,894 A | 2/1987 | Porter et al. | |

(Continued)

FOREIGN PATENT DOCUMENTS

| | | | |
|---|---|---|---|
| CA | 2540044 A1 | 4/2005 | |
| EP | 294993 A1 | 12/1988 | |

(Continued)

OTHER PUBLICATIONS

"The Elizabeth Companies Tablet Design Training Manual" (Elizabeth Carbide Die Co., Inc., p. 7 (McKeesport, Pa.), Jul. 3, 2003.

(Continued)

*Primary Examiner* — Aradhana Sasan

(57) ABSTRACT

A dosage form comprising a tablet core and one or more discontinuous coated regions in various configurations on the surface of the dosage form is disclosed. A method for making the dosage form is also disclosed.

9 Claims, 36 Drawing Sheets

(51) Int. Cl.
   *B05D 1/26* (2006.01)
   *B05C 1/00* (2006.01)

(56) References Cited

U.S. PATENT DOCUMENTS

| | | |
|---|---|---|
| 4,683,256 A | 7/1987 | Porter et al. |
| 4,725,441 A | 2/1988 | Porter et al. |
| 4,802,924 A | 2/1989 | Woznicki et al. |
| 4,820,524 A | 4/1989 | Berta |
| 4,828,841 A | 5/1989 | Porter et al. |
| 4,867,983 A | 9/1989 | Berta |
| 4,873,231 A | 10/1989 | Smith |
| 4,906,478 A | 3/1990 | Valentine et al. |
| 4,966,771 A | 10/1990 | Berta |
| 5,089,270 A | 2/1992 | Hampton et al. |
| 5,213,738 A | 5/1993 | Hampton et al. |
| 5,234,099 A | 8/1993 | Berta |
| 5,275,822 A | 1/1994 | Valentine et al. |
| 5,317,849 A | 6/1994 | Sauter |
| 5,415,868 A | 5/1995 | Smith et al. |
| 5,424,075 A | 6/1995 | Daher et al. |
| 5,464,631 A | 11/1995 | Hoover et al. |
| 5,510,385 A | 4/1996 | Stroppolo et al. |
| 5,534,263 A | 7/1996 | Wong et al. |
| 5,630,871 A | 5/1997 | Jordan |
| 6,103,260 A | 8/2000 | Luber et al. |
| 6,274,162 B1 | 8/2001 | Steffenino |
| 6,365,183 B1 * | 4/2002 | Edgren ............. A61K 9/2072 424/464 |
| D500,849 S | 1/2005 | Rinker |
| D506,544 S | 6/2005 | Rinker |
| D525,356 S | 7/2006 | Rinker |
| 7,217,381 B2 | 5/2007 | Sowden |
| 7,638,081 B2 | 12/2009 | Clarke et al. |
| 7,879,354 B2 | 2/2011 | Rinker et al. |
| 8,067,029 B2 | 11/2011 | Rinker et al. |
| 8,101,244 B2 | 1/2012 | Clarke et al. |
| 8,122,149 B2 | 2/2012 | Ingle et al. |
| 8,123,509 B2 | 2/2012 | Clarke et al. |
| 8,252,234 B2 | 8/2012 | Clarke et al. |
| 8,815,290 B2 | 8/2014 | Rinker et al. |
| 8,967,074 B2 | 3/2015 | Clarke et al. |
| 8,986,777 B2 | 3/2015 | Clarke et al. |
| 2004/0191499 A1 | 9/2004 | Hallett |
| 2006/0147585 A1* | 7/2006 | Winckelmann ......... B05B 14/10 426/96 |
| 2007/0065364 A1* | 3/2007 | Oshiack ............... A61K 9/1694 424/10.1 |
| 2012/0045510 A1 | 2/2012 | Waldman |
| 2015/0190834 A1 | 7/2015 | Clarke et al. |
| 2016/0032909 A1 | 2/2016 | Fiesser et al. |

FOREIGN PATENT DOCUMENTS

| | | | |
|---|---|---|---|
| EP | 448231 A1 | 9/1991 | |
| EP | 607009 A1 | 7/1994 | |
| WO | WO 99/56730 A1 | 11/1999 | |
| WO | WO 2006/099618 A1 | 9/2006 | |
| WO | WO 2009/051794 A1 | 4/2009 | |
| WO | WO-2016038356 A1 * | 3/2016 | ........... B29C 64/118 |

OTHER PUBLICATIONS

USP 24, 2000 Version, 19-20 and 856 (1999).
Leiberman et al., Pharmaceutical Dosage Forms—Tablets, vol. 2, 2nd ed., Marcel Dekker Inc., 1990, pp. 213-217, 327-329.
PCT/US2017/042557 International Search Report dated Mar. 2, 2018.

* cited by examiner

COMPRESSED CAPLET
VOLUME: 0.0288 IN^3

VERTICALLY (LONGITUDINALLY) COMPRESSED TABLET
VOLUME MATCHED TO
CAPLET VOLUME (SHOWN LEFT): 0.0288 IN^3
LENGTH TO DIAMETER RATIO L/D: 2.648
(COMPARED TO 2.876 OF NO. 1 CAPSULE)

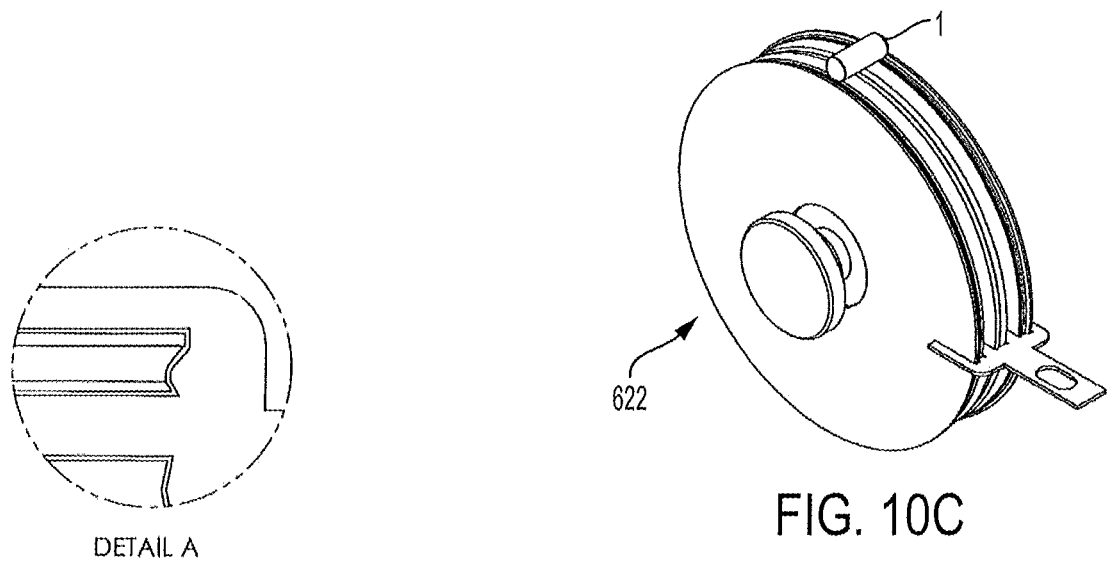
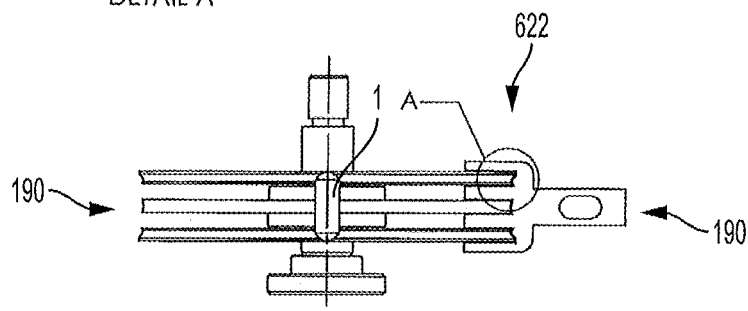
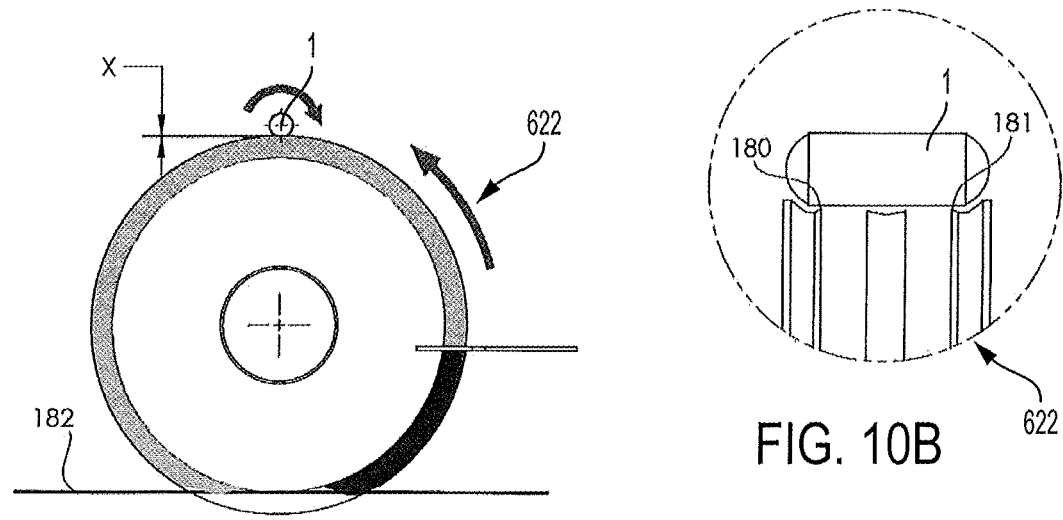
FIG. 10C
FIG. 10B
FIG. 10A

MACHINE BASE NOT SHOWN

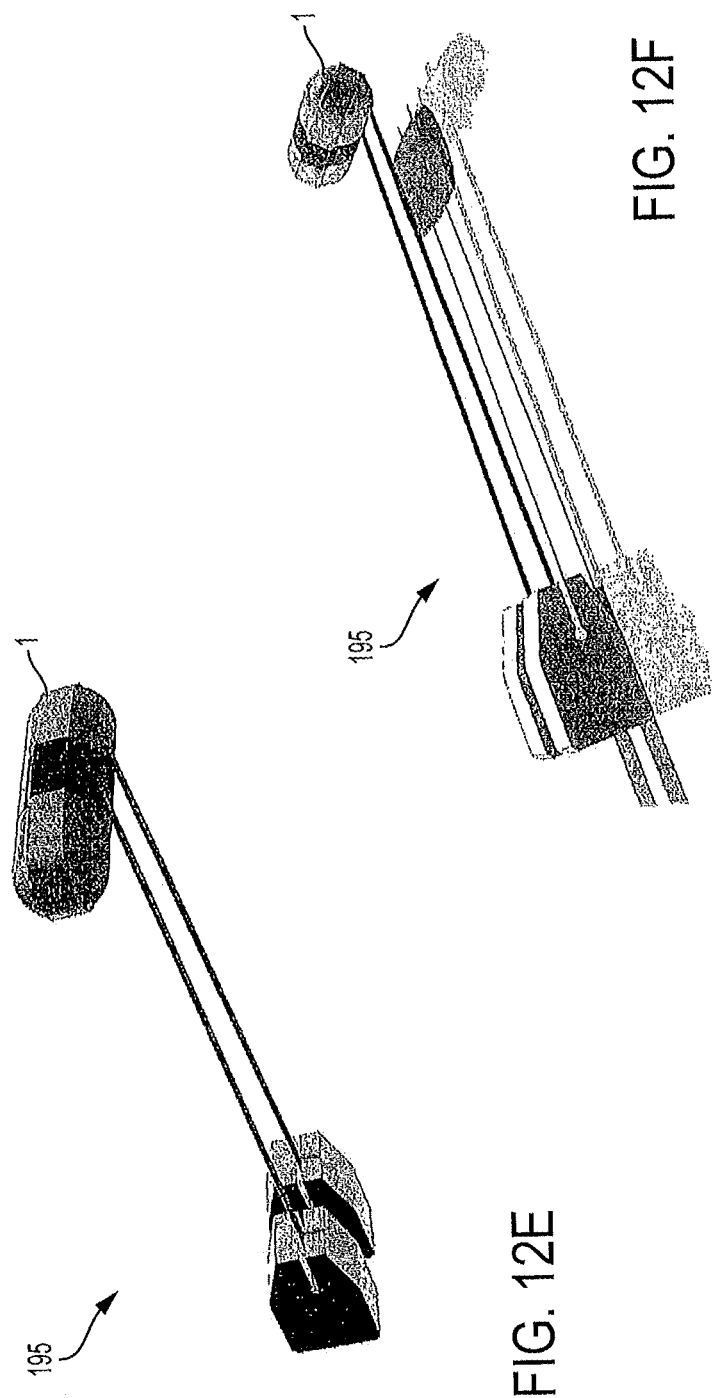

TABLETS HAVING DISCONTINUOUS COATED REGIONS

CROSS REFERENCE TO RELATED APPLICATIONS

This application is a divisional of U.S. application Ser. No. 15/652,315, filed Jul. 18, 2017, which claims priority of the benefit of the filing of U.S. Provisional Application Ser. No. 62/364,059, filed Jul. 19, 2016, the contents of which are hereby incorporated by reference in their entirety.

FIELD OF THE INVENTION

The present invention relates to a dosage form comprising a tablet core, preferably in compressed form, that has a coating over a portion of its exterior surface. The coating preferably is in the form of one or more discontinuous coated region. The one or more discontinuous coated regions appear on the dosage form in various configurations. The one or more discontinuous coated regions confer a number of benefits to the dosage form including, but not limited to, the ability to add actives, colors, flavors, sensates and textures; improved swallowability; perception of speed, taste masking, and visual recognition to aid in product selection. The present invention also relates to apparatus that may be used to apply the one or more discontinuous coated regions on the dosage form.

BACKGROUND OF THE INVENTION

Capsules had long been recognized as a preferred dosage form for the oral delivery of active ingredients, which may be in the form of powder, liquid or granules of different compositions, for delivery to the gastro-intestinal tract of a human. Advantages of capsules as a dosage form include the variety of shapes and color combinations (including different colored caps and bodies), enhancing their unique identification, their glossy elegant appearance, and their easy swallowability. One type of commonly used capsule is a two-piece hard shell capsule, typically made from gelatin, starch, or cellulose derivatives. The hard shell capsule typically comprises a longer body having an outside diameter, and a relatively shorter cap having an inside diameter that will fit over the outside diameter of the body. The cap fits snugly over the body, creating an overlapping portion of the capsule.

In view of the tamperability of old-fashioned capsules made with hard shell capsule halves of different diameters which can be taken apart, steps have been taken since the 1980s, to manufacture capsule shells which, once assembled, cannot be disassembled without their destruction. One such example is the Capsugel CONI-SNAP® capsule, which has grooves that lock the cap and body together after the capsule has been filled. Another such example is the Parke-Davis KAPSEAL® capsule, in which the body and cap are sealed together using a discontinuous coated region of gelatin. Although the sealing or discontinuous coated banding of capsule shell halves has, in a large part, proven effective to at least make tampering evident to the consumer, some companies have preferred to manufacture solid dosage forms having densely compacted cores to further reduce the possibility of tampering.

One of the first types of film-coated elongated compressed tablets was referred to as a "caplet". The caplet form offered enhanced swallowability over uncoated tablets due to its elongated shape. While caplets are still popular today, the next generation of dosage forms, which offered all of these advantages of the capsule, comprised densely compacted cores that were coated with gelatin or similar glossy materials, typically in two parts having different colors. U.S. Pat. Nos. 5,089,270; 5,213,738; 4,820,524; 4,867,983 and 4,966,771 represent different approaches to providing a capsule-shaped product in the form of an elongated tablet having a coating, which provides the appearance and, therefore, the consumer acceptability of the previously popular capsule.

U.S. Pat. Nos. 5,415,868 and 5,317,849 disclose different manners by which either hard shell capsule halves can be shrink-wrapped onto a tablet (the '868 patent) or a tablet core covered at opposite ends with a soft gelatin capsule shell half and subsequently dried to simulate a capsule-like medicament (the '849 patent). U.S. Pat. No. 5,464,631 discloses that studies have also shown the functional importance to consumers of providing a capsule-appearing solid dosage form, which is multi-colored. The utilization of two colors functionally identifies the type of medication as well as provides a capsule-appearing product with a psychologically perceived medicinal efficacy. Aesthetically, also, consumers apparently prefer the attractive appearance of multi-colored capsules to single colored capsules.

For purposes of the invention, a gelatinous material is defined to be a material that, when applied to a surface of a dosage form, produces a film coating having a surface gloss comparable to gelatin coatings. Preferably, the gelatinous coating has a surface gloss greater than about 150, more preferably greater than about 200.

Gelatins have served as coating material. Hence, the phrase "gelatinous" material. Work has been done to expand the range of materials capable of providing the desired glossy finish that contain substantially no gelatins.

U.S. Pat. Nos. D500,849; D506,544; D525,356; 7,879,354; 8,067,029; and U.S. Pat. No. 8,815,290 to Johnson & Johnson Consumer Inc. disclose a dosage form that comprises a core having an exterior surface and first and second ends and comprising one or more active ingredients; a first gelatinous coating over at least part of the core; and a second gelatinous coating over at least part of the core.

U.S. Pat. No. 5,534,263 to Alza Corporation discloses a dosage form that is useful for prolonged delivery of an active agent. The dosage form is a matrix with two or more insoluble bands on its surface. The reference discloses that, according to an embodiment, the two or more bands drop off the matrix as it erodes, and that according to another embodiment, the surface area between the two or more bands, which are fixed on the matrix, erodes.

Canadian Patent No. 2,540,044 to Alza Corporation discloses a dosage form that provides controlled release of an active agent. The reference discloses that the dosage form contains a reservoir that contains active; an engine partially within the reservoir; and a soluble or insoluble band provided over an outer surface of the engine and the reservoir that binds the engine to the reservoir.

International Published Application No. WO2006099618 to Dr. Reddy's Laboratories Ltd. discloses a dosage form that comprises a substrate containing an active agent and a solid component deposited onto areas of a surface of the substrate that also contains an active agent. The reference discloses that the solid component may contain pharmaceutically acceptable excipients, including, e.g., colorants, flavors, taste-masking agents and the like. The reference discloses that according to an embodiment, a band may be applied to the surface and that areas on the surface that receive the band may be recessed. According to an embodiment, a band surrounds the circumference of a tablet.

U.S. Pat. No. 8,252,234 to Smithkline Beecham Corporation discloses an apparatus for producing a pharmaceutical product that contains a dose inspection device, wherein the dose inspection device performs optical profilometry on a carrier substrate to determine an amount of active ingredient that has been added to the carrier substrate.

U.S. Pat. Nos. 8,122,149 and 8,101,244 to SmithKline Beecham Corporation discloses an apparatus for producing a pharmaceutical product that contains a dose inspection system, wherein the dose inspection system contains a camera, wherein the camera takes an image of a dosage of active agent while being applied to a carrier substrate.

U.S. Pat. Nos. 8,123,509 and 7,638,081 to SmithKline Beecham discloses a mold that contains a cavity in which a core may be located, wherein the core has a space to define a shape and dimension of coating to be placed on the core.

U.S. Published Applications Nos. 20160032909 and 20150190834 to Glaxo SmithKine disclose a method and a device for dispensing fluid from a pump that includes dispensing a first volume of fluid through an outlet port to form a pendant droplet in the outlet port; dispensing a second volume of fluid though the outlet port; and ejecting a full droplet from the outlet port, wherein the full droplet volume is the sum of the first droplet volume and the second droplet volume.

U.S. Pat. Nos. 8,986,777 and 8,967,074 to SmithKine disclose a device for dispensing a fluid onto a target that contains a porous band having a hollow interior positioned so that the end of the dispensing nozzle is in the hollow interior to form a gap between the inner surface of the hollow band and the end of the dispensing nozzle.

There continues to be a need in the pharmaceutical industry to provide over-the-counter coated dosage forms which simulate the appearance of capsules and which identify the source and type of medication provided so that the consumer can readily identify, for example, if the product is a particular type of analgesic or whether it includes antihistamines or other active ingredients in combination with analgesics. Such solid dosage forms have preferably been in the shape of an elongated tablet, and are identified as gelcaps when a solid elongated core is covered with a gelatinous covering or geltabs where the core is in the shape of a round tablet with a gelatinous coating.

The present invention furthers these earlier advances by producing an improved gelcap or geltab relative to the commercially available gelatinous coated products.

In accordance with the invention, gelatinous discontinuous coated regions are used to provide similar benefits as coating, while providing a new appearance and the ability to vary the types of materials used in the discontinuous coated regions, preferentially on a compressed or coated compressed dosage form. Use of the discontinuous coated regions in accordance with the invention provides advantages, including but not limited to, permitting the addition of actives, colors, flavors, sensates and textures; improving swallowability; providing a perception of speed; permitting taste masking; and providing for visual recognition to aid in product selection.

SUMMARY OF THE INVENTION

Tablet compression and coating are two of the most critical aspects of pharmaceutical dosage form manufacturing, since these are the main aspects of the product discernable to the patient consuming the product. Tablet compression tooling is typically designed to produce tablets free of visual defects to the extent permitted by the composition of the tablet and the equipment used in the manufacturing process. Identifying marks and symbols engraved into the tablet surface during compression are generally designed in adherence with established guidelines for shape, size, depth, wall angles, corner rounding, spacing, etc. of the characters to minimize the introduction of defects into debossed designs and to produce legible identification on the tablet following compression and/or coating. In its desired form, batch tablet coating is performed in a manner yielding a homogenous coating appearance free of visual defects and irregularities. When properly applied, conventional tablet coating equipment (e.g., coating pans, fluidized bed coaters, etc.) are designed to minimize heterogeneity of the resultant coated tablets, and post-coating processing, including, but not limited to, surface printing, gelatin dipping, overlayer placement, and laser drilling, is required to introduce, or give the appearance of, heterogeneous regions on the tablet surface.

The dosage form of the invention may be coated using methods including, but not limited, to carrier tray coating, spray coating, dip coating, enrobing, electrostatic deposition and/or 3D printing.

The techniques described herein provide a demonstrated method of preparing solid dosage forms on conventional tablet preparation equipment containing visually identifiable features on the tablet surface that will intentionally produce heterogeneous regions of coating deposition upon conventional tablets.

Other features and advantages of the present invention will be apparent from the detailed description of the invention and from the claims.

BRIEF DESCRIPTION OF THE DRAWINGS

For example, a movable surface with a non-circular geometry may be employed as a "coating wheel" to better coat substrates having corresponding non-circular geometry. A face of the movable surface can have any configuration to assist with corresponding tablet having varied configuration. FIGS. 6C and 6D are diagrams of the fixture apparatus 620 and conformal coating wheel 621. When movable pins FIG. 6D, 630 engage into the depressed features 603*a* and 603*b* of the standard convex tablet 601 an axis of rotation is enabled. The rotation of conformal coating wheel 621 which is covered in coating solution (not shown) induces rotation and subsequent circumferential application of material onto the standard convex tablet 601. The shear behavior of the coating fluid (not shown), the shear rate which is determined by the rotational speed and diameter of the conformal coating wheel 621 and the viscosity of the coating solution (not shown) create a force which induces rotation of the standard convex tablet 601.

FIGS. 10A-10C are diagrams showing a segmented coating wheel 622, which contains one or more drive rings FIG. 10B, 180 and 181, that can be used in combination with carrier trays 190 and a bath FIG. 10A, 182 to apply one or more circumferential discontinuous coated regions (not shown) to a dosage form in accordance with an embodiment of the invention.

FIG. 10B shows drive ring 180 and 181 features. The purpose of the drive rings 180 and 181 are to disrupt the boundary fluid layer and create a means to achieve rotation of the standard caplet 1. Without these drive rings 180 and 181, the hydrostatic effect of the fluid film acts similar to a fluid bearing which can prevent proper rotation. The drive rings 180 and 181 minimize this effect by piercing the fluid and creating mechanical engagement with the standard caplet 1.

As the standard caplet 1 is conveyed by means of the carrier tray 190 into proximity of the segmented coating wheel 622 the coating fluid 182 which is distributed around the circumference of the segmented coating wheel 622 begins to coat the standard caplet 1. The rotation of the segmented coating wheel 622 and the shear force induced by the viscosity of the coating fluid 182 induces rotation of the standard caplet 1 and subsequent circumferential discontinuous coated region coating of the standard caplet 1. The lift height "X", the diameter of the segmented coating wheel 622 and the linear velocity of the carrier tray 190 determine the rotational velocity of the standard caplet 1 and the duration of time the standard caplet 1 is rotated.

Figure 11:
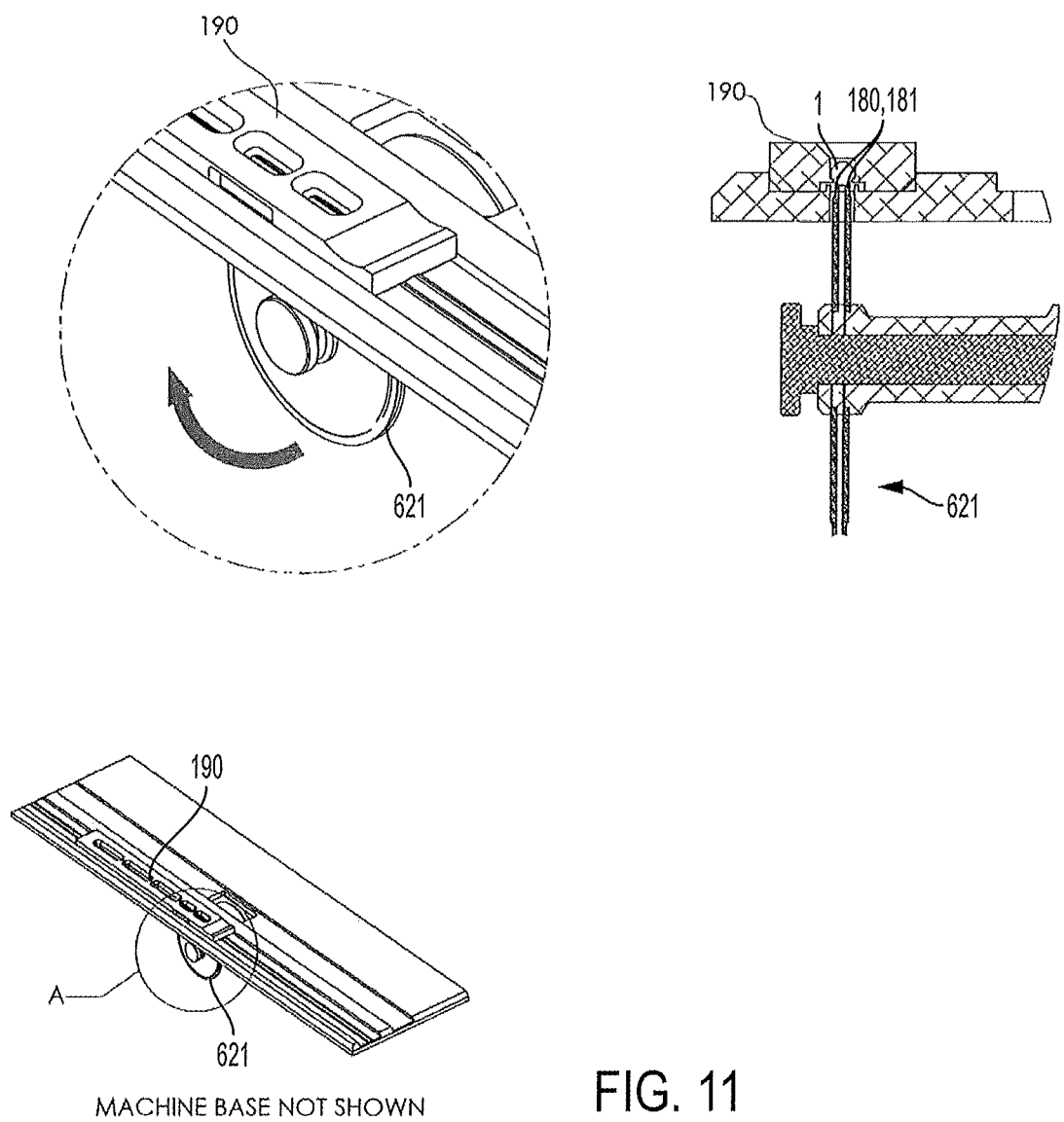

FIG. 11 is a diagram showing a coating wheel 621 that can be used in combination with a carrier tray 190 and the drive rings 180, 181 to apply one or more longitudinal discontinuous coated regions (not shown) to a dosage form in accordance with an embodiment of the invention.

Figure 12A:
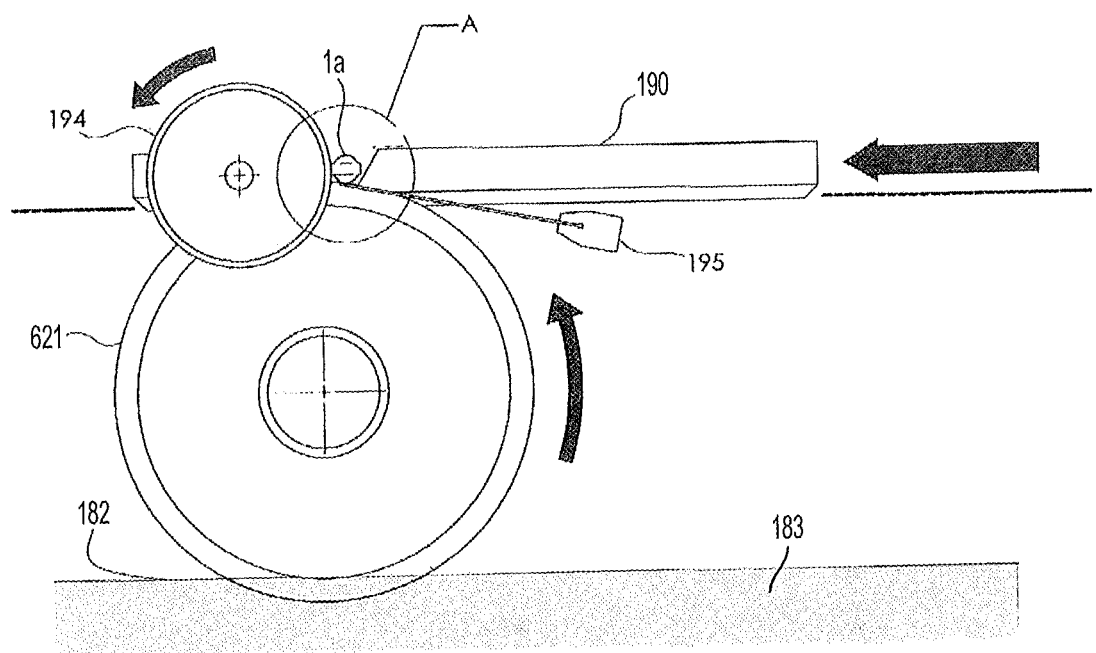
Figure 12B:
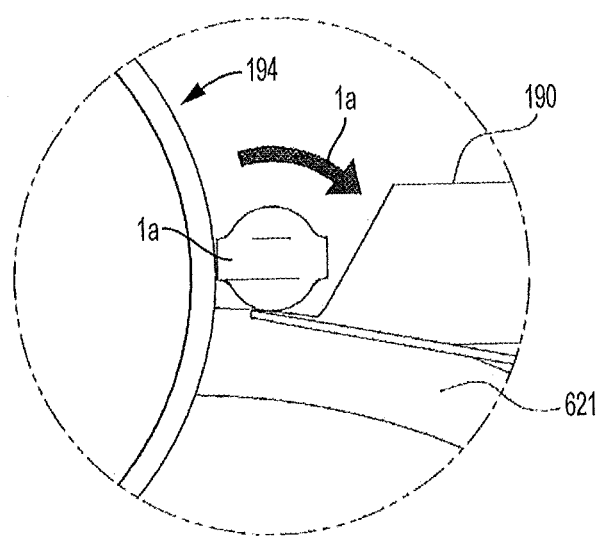
Figure 12C:
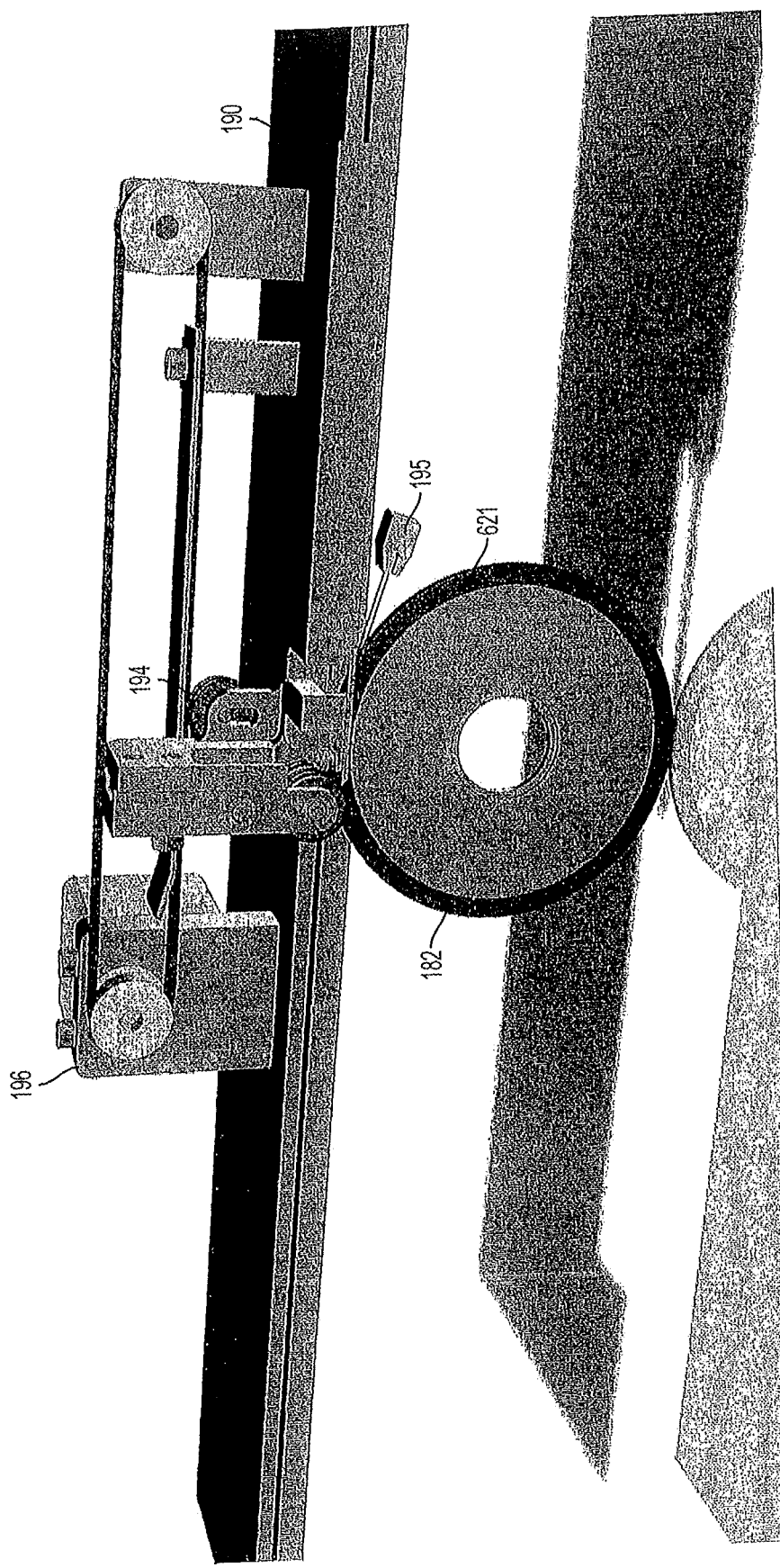

FIGS. 12A-12G are diagrams showing an embodiment that permits coating of non-rounded horizontally compressed caplets 1*a*. FIG. 12A shows the carrier tray 190, the conformal coating wheel 621, which contains one or more drive rings (not shown), and the coating fluid bath 182 in action. The conformal coating wheel 621 dips into the coating fluid bath 182 containing coating fluid 183. A roller wheel 194, also known as a moving abutment face, which runs along the conformal coating wheel 621 prior to the carrier tray 190, may be employed to assist with rolling of non-rounded caplets 1*a*. The carrier tray 190 moves along the edge of the conformal coating wheel 621 to permit coating of a portion of the non-rounded caplet 1*a*. A capillary filament holder 195 can be employed to ensure a straight coated area with clean edges. FIG. 12B shows direction of rotation of a non-rounded caplet 1*a* when the carrier tray 190, the conformal coating wheel 621 and the coating bath (not shown) are in action. FIG. 12C shows a means for driving the roller wheel 194 using a motorized friction belt system 196.

Figure 12D:
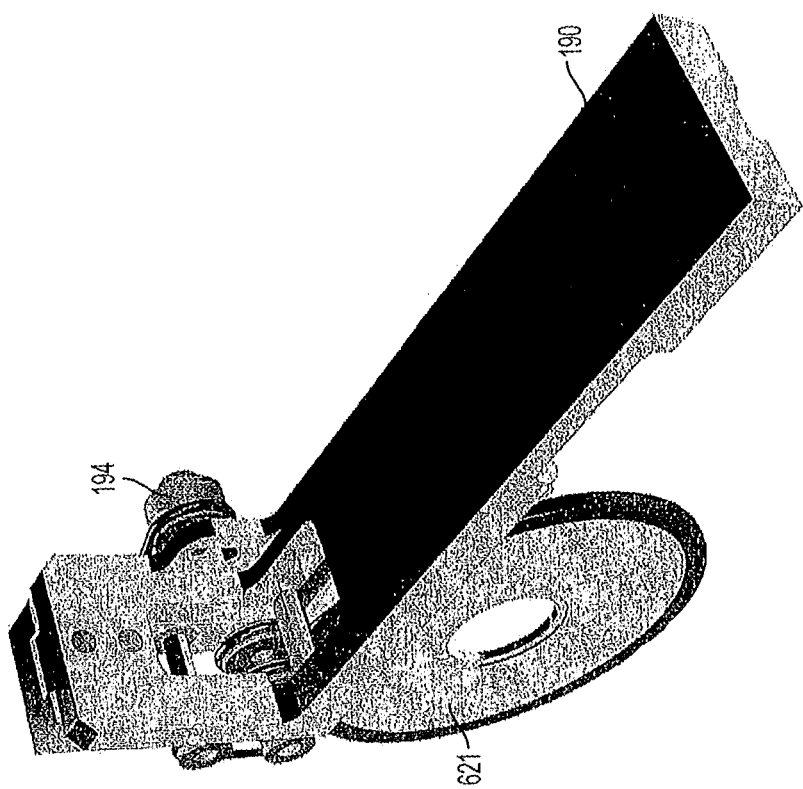
Figure 12G:
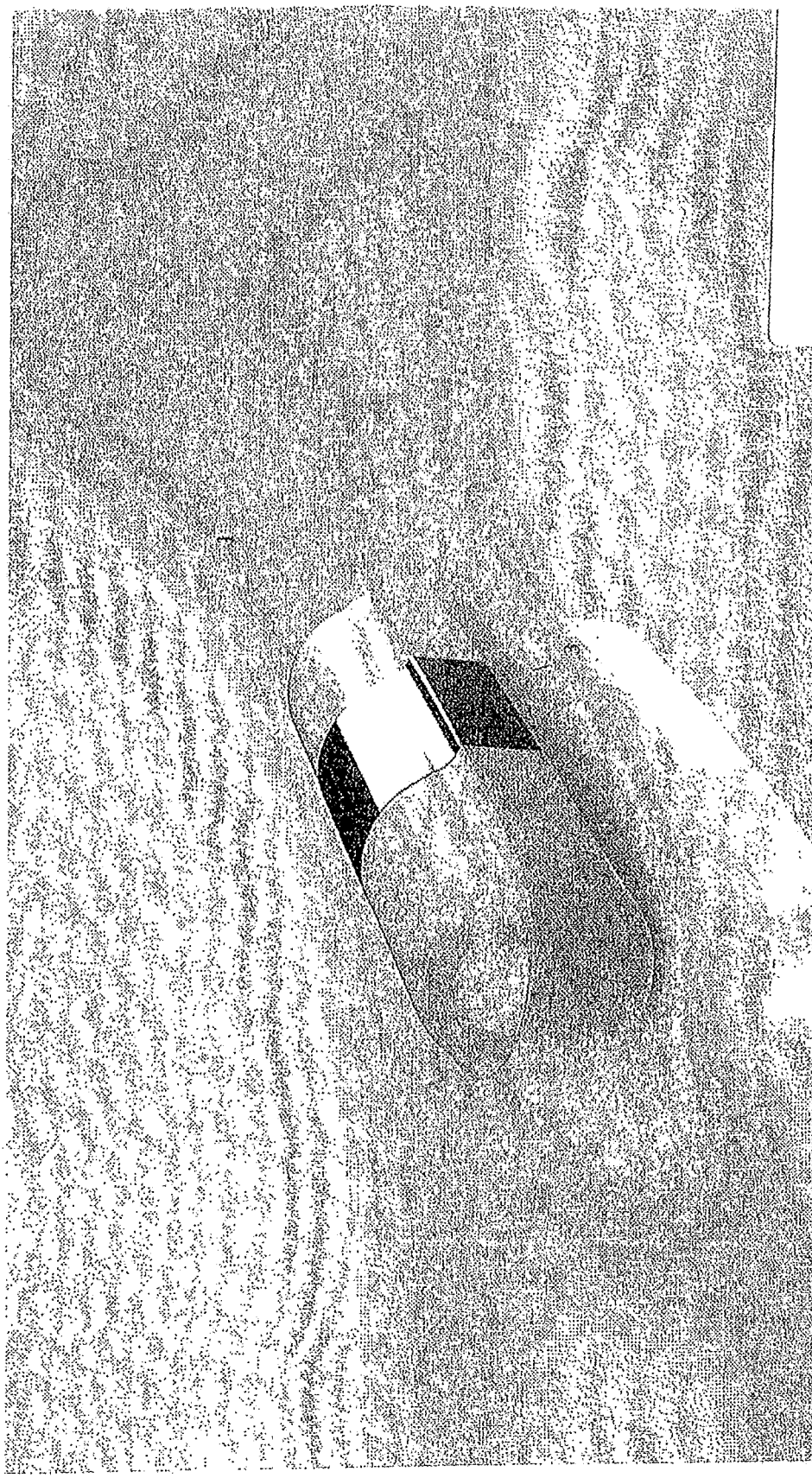

FIG. 12D shows the carrier tray 190 with roller wheel 194 without the motorized friction belt system 196. FIGS. 12E and 12F show the capillary filament holders 195 which help to create a straight and uniform edge of the discontinuous coated region by using capillary action to distribute the coating fluid over the peaks and valleys on the non-circular cross section of the horizontally compressed caplet. FIG. 12G shows a dosage form prepared in accordance with the embodiment(s) set forth in FIGS. 12A-12-F.

In the embodiments of this invention described thus far, the geometry of the coating discontinuous coated regions are constrained by tablet and caplet geometry, the direction of feed that the tablet or caplet is presented to the coating wheel and the geometry of the coating wheel itself. In order to remove these restrictions of coating geometry and to improve the accuracy of the amount of coating applied for surface application of drug, an alternate embodiment of the invention has been developed. In this embodiment an intermediate applicator has been designed to both accurately control the volume of coating material and to independently control the geometry of the coating on the tablet. Since the shape of the applicator, a circle, square or polygon for example, can be selected independently from the shape of the tablet, greater freedom and precision of coating are obtained. For the application of one or more drugs to regions on the surface of a tablet or gum, precise control of the coating fluid dose weight is of paramount importance to be in compliance with pharmaceutical regulation, i.e., cGMP guidelines. In order to aid in the goal of high precision dose accuracy, a feature of a preferred embodiment of the invention is use of volumetric spacing features on the surface of the applicator. These features when engaged against a tablet/caplet housed in a spring loaded carrier assure that a fixed volume of drug containing coating is deposited during each application. Since the tablet is contained in a spring loaded and floating carrier, size variations which are commonly encountered in manufacturing are negated and therefore do not adversely affect the dose accuracy.

Figure 13A:
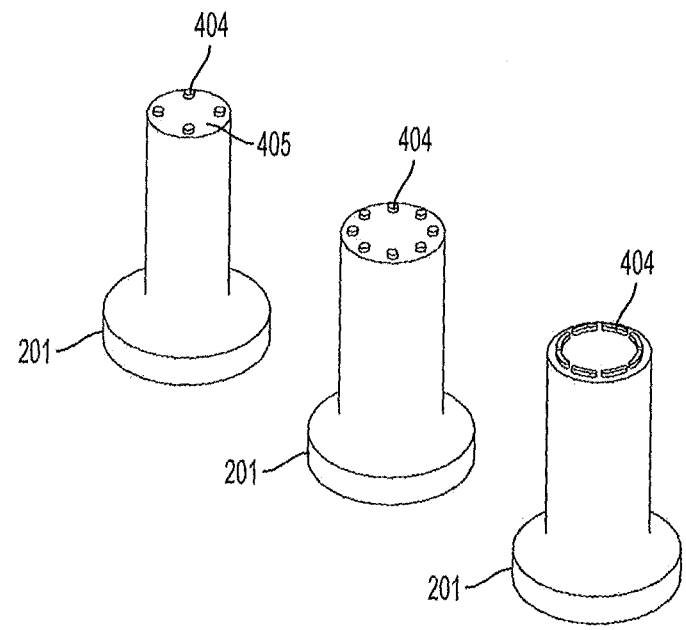
Figure 13B:
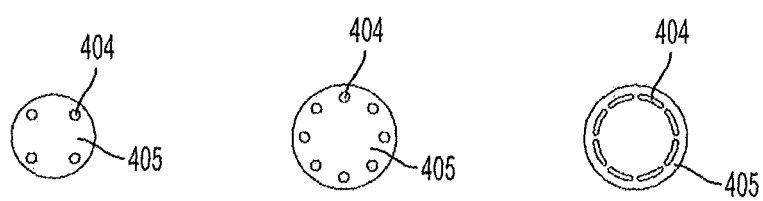
Figure 13C:
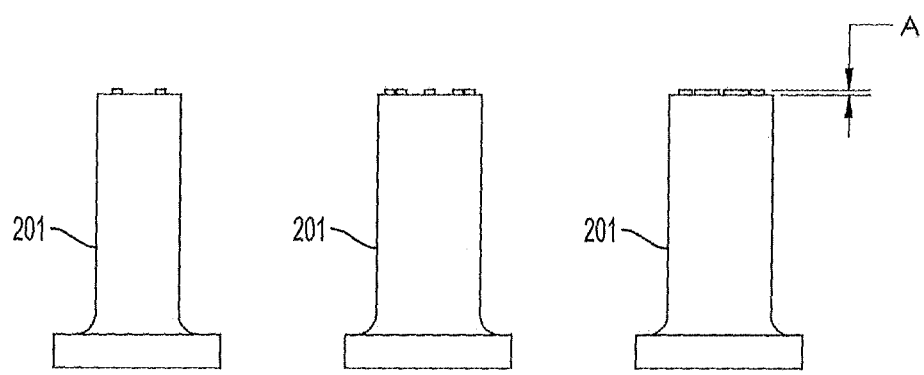

FIGS. 13A-13C are diagrams of intermediate applicator geometries. FIG. 13A-FIG. 13C are views of circular intermediate applicators 201 showing arrangements of volumetric spacing features 404. Of note with these arrangements is that the geometries are vented such that when charged with fluid the entrained air can escape between the volumetric spacing features 404. (An enclosed ring would entrap an air bubble so this geometric arrangement was created to prevent this occurrence.) The surface area ($\pi r2$ in the case of circular geometries) of the applicator and the length "A" of the volumetric spacing features 404 are selected to control the volume of fluid coating material. Surface tension of the fluid around the volumetric spacing features 404 create a leveling effect which also contributes to uniformity of fluid distribution across the face of the applicator 405 and aids in achieving accurate dosing.

Figures 14A, 14B, 14C:
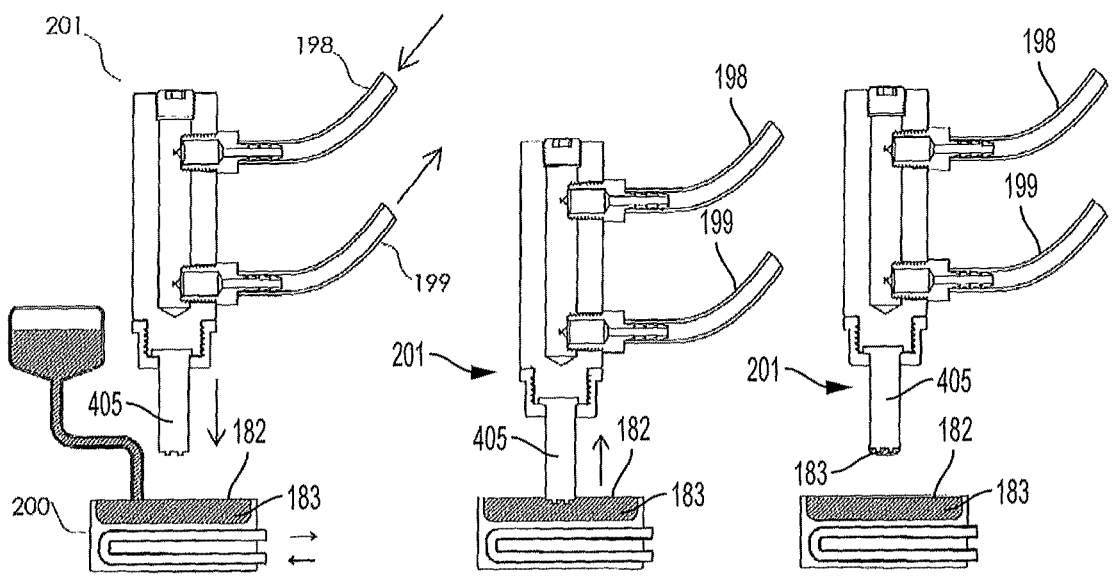
Figures 14D, 14E, 14F:
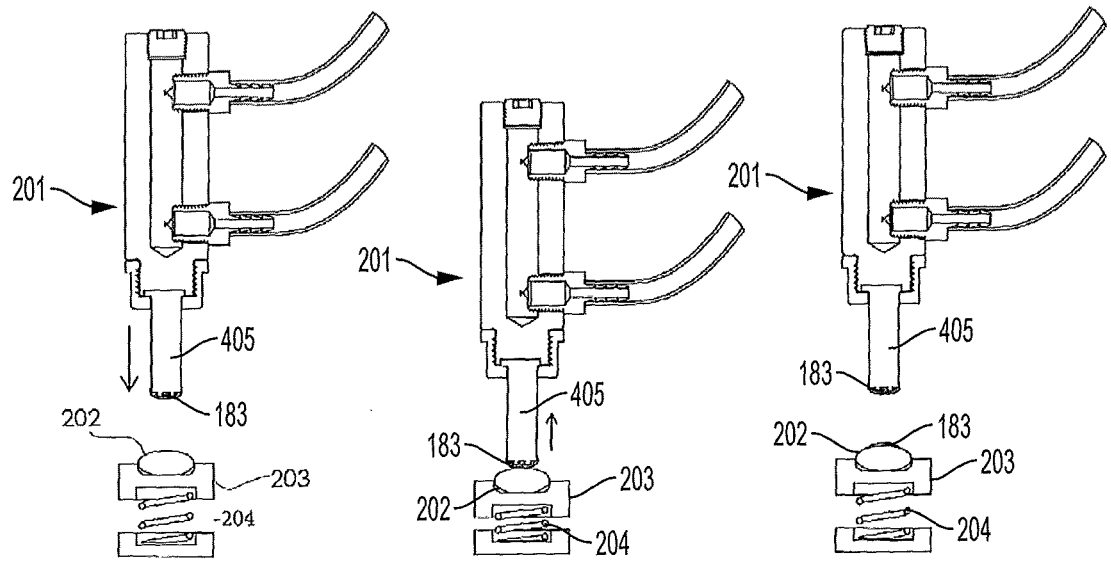

FIGS. 14A-14F outline the sequence of steps for charging the intermediate applicator 201 with fluid and depositing the fluid onto the surface of the tablet or gum medicament 202. FIG. 14A depicts a heated coating fluid bath 182 with an inner bath that establishes an accurate and constant fluid level established by the outlet of the coating fluid reservoir 183. Intermediate applicator 201 is heated by means of fluid connections 198 and 199. FIG. 14B depicts intermediate applicator 201 being immersed into the coating fluid bath 182 up to the surface 405 of the intermediate applicator 201. FIG. 14C shows the intermediate applicator 201 now charged with fluid at the surface 405 of the intermediate applicator 201. FIG. 14D depicts a tablet or gum medicament 202 seated in a spring loaded carrier 203. The carrier spring loaded 203 and spring 204 are designed to compress as well as accommodate angular misalignment such that the tablet or gum medicament 202 can seat against the intermediate applicator 201 regardless of surface imperfections or seating irregularities. FIG. 14E depicts the intermediate applicator 201 compressing the tablet or gum medicament 202 against the spring 204 thus assuring that the volumetric spacing features 404 control the gap and therefore the volume and geometric distribution of coating fluid 183 on the surface of the tablet or gum medicament 202. Any object(s) that permit(s) axes of freedom such that the surface of the tablet or gum medicament 202 conforms to the volumetric spacing features 404 is envisioned to be within the scope of the present invention. FIG. 14F depicts the intermediate applicator 201 after fluid application. In general, for most coating fluids 183 and most non-absorbent tablets or gum medicaments 202 half of the coating fluid 183 remains on the intermediate applicator 201 and half of the coating fluid 183 is deposited on the surface of the tablet or gum medicament 202 as a discontinuous coated region [ ]. Since the fluid viscosity is controlled and unchanging this is highly repeatable and factored into the dose calculations. Absorbent tablets or gum medicaments 202 would deviate from this 50:50 ratio depending on the absorbency of the tablet or gum medicament 202 material and the duration of time that the applicator remains in contact with the surface.

Figure 15:
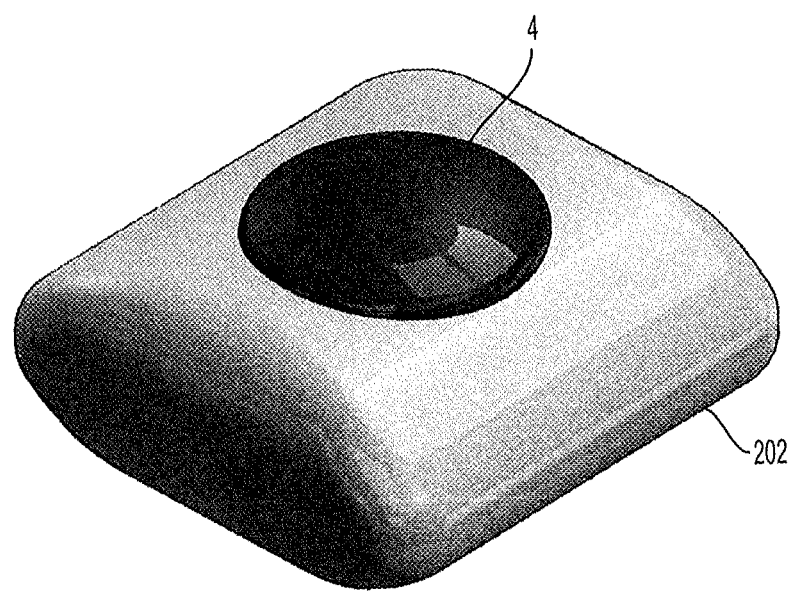

FIG. 15 is a diagram of a dosage form coated using the embodiment disclosed in FIGS. 14A-14F.

Figure 16:
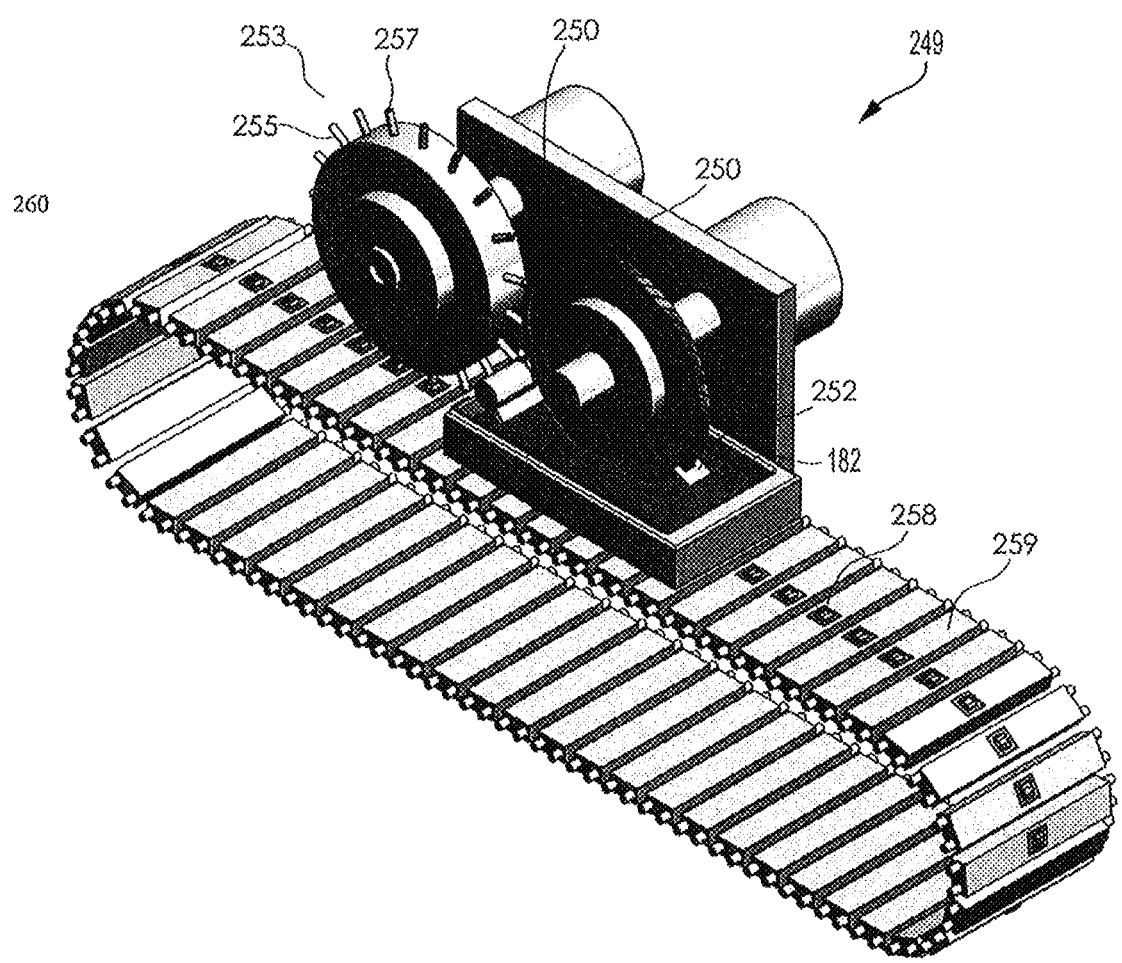

FIG. 16 is a diagram of a high speed continuous motion coating apparatus 249 using an alternate embodiment of the intermediate applicator coating method. In FIG. 16, a single lane of medicaments 258 is shown being coated for clarity; however a production scale implementation could have multiple lanes of product for higher outputs. In this embodiment, the challenge of getting fluid from a stationary coating bath onto a continuously moving applicator and a continuously moving conveying system containing tablets/gums is addressed. In this embodiment, a rotary fluid transfer wheel 250 is introduced. This rotary fluid transfer wheel 250 is immersed into coating fluid bath 182 with a dose adjust doctor blade 252. The dose adjust doctor blade 252 is adjusted to control the amount of fluid coating the rotary fluid transfer wheel 250 which picks up a coating of fluid on its circumference as it rotates in the coating fluid bath 182. The rotary fluid transfer wheel 250 is synchronously connected to applicator wheel 253 such that at the fluid transfer zone 254 the tangential velocities of the two wheels are matched. The applicator wheel 253 has applicators 255 that are on a circular pitch that precisely matches the pitch of the tablet conveyor 260. The applicator wheel 253 is also synchronously connected to the tablet conveyor 260 such that the applicator tips 257 precisely line up with the tablet or gum medicaments 258 contained in the conveyor links 259.

Figure 17:
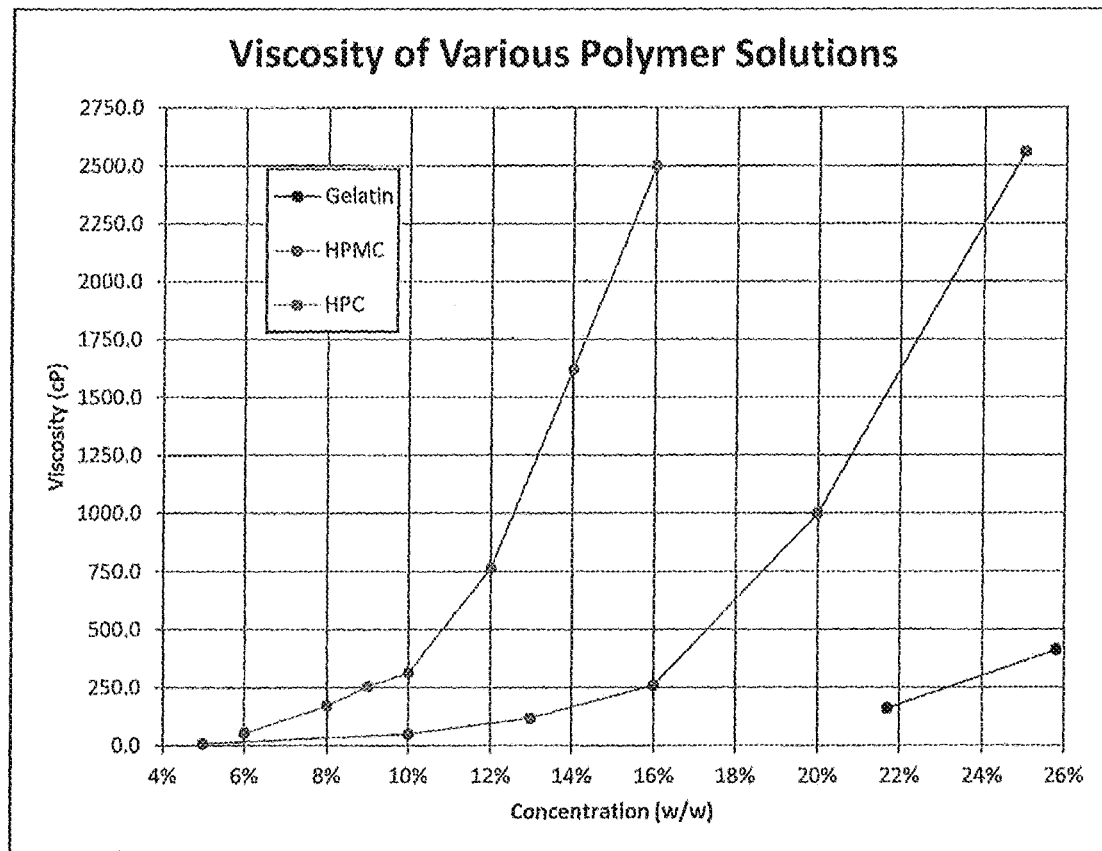

FIG. 17 is a graph showing the results of the viscosity testing for Examples 1-3.

Figure 18:
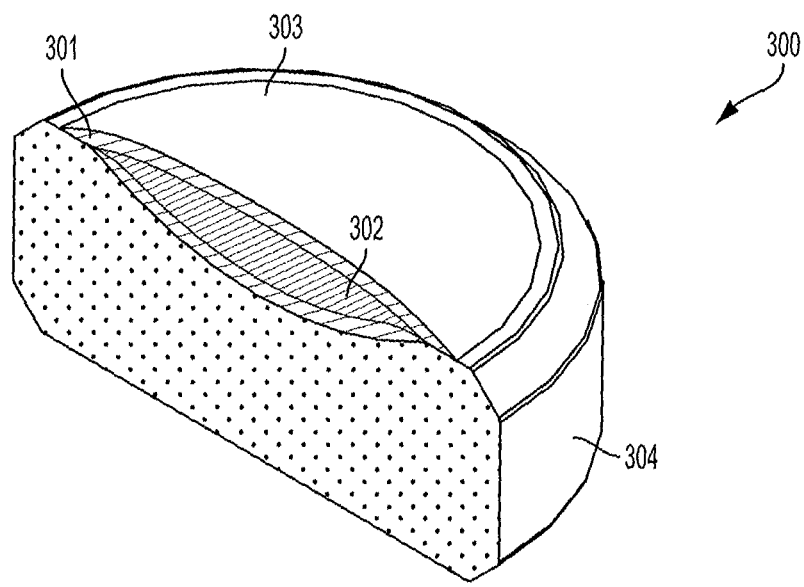
Figure 19:
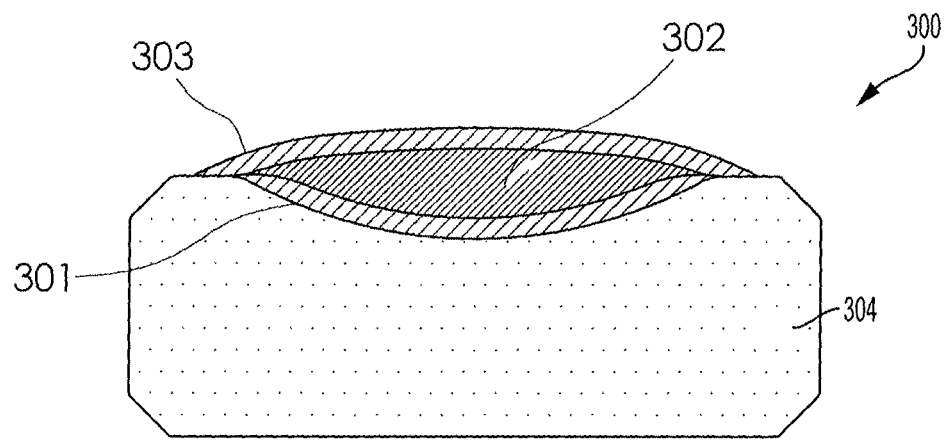

FIGS. 18 and 19 illustrate a cross sectional view of an embodiment of the invention where a dosage form 300 is constructed with three layers of material 301, 302, and 303 which are applied to the surface of a substrate 304 in a series of sequential steps using several applicator systems. Each layer of material that is applied to the substrate (e.g., tablet, gum or lozenge) may have distinct physical properties such as, e.g., level of solubility, density, flavor, opacity/translucence, and color. Different active agents, flavors or sensates can be contained in each layer and incompatible active agents, flavors or sensates can be separated by an intermediate barrier layer. In combination with the manipulation of the solubility of the carrier material the release profile of the various layers can each be individually controlled. For example, a burst release effect can be achieved when an erosion matrix tablet, gum or lozenge is coated with an immediate release layer of material which is subsequently encapsulated or overcoated by an erosion or slowly soluble outermost layer. When either the outermost later or the erosion matrix tablet is dissolved to the point where the immediate release layer is exposed, this layer can quickly solubilize to create the desired burst release effect. In the case of a gum or lozenge, saliva would be the solubilizing fluid and the bust release would occur in the mouth. In the case of a swallowable dosage form, gastric fluids would be the solubilizing agent and the bust release would occur in the stomach.

In summary, the use of the applicator system allows each layer to have a different pattern, a different thickness, a different volume and a different surface area to control both the appearance and level of encapsulation of the preceding layer or layers. The layers are not constrained to be of uniform thickness or to cover continuous areas as is common with conventional pharmaceutical coating technologies such as pan coating and enrobing. The use of an applicator system having volumetric spacing features enables precision and control of fluid dosing and fluid volume. This, in combination with chilled active agent can create a rapid set molded region.

Figure 20:
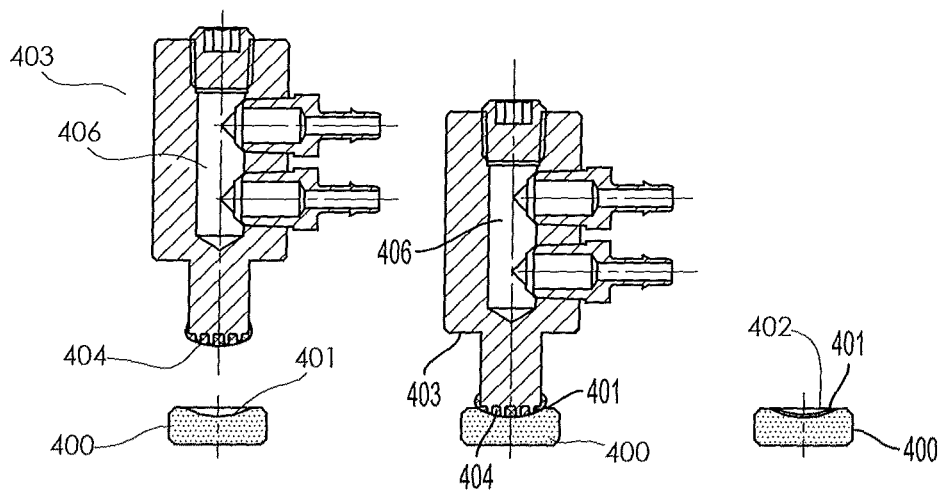

FIGS. 20-30 illustrate the use of several applicator systems to prepare the dosage form described in FIGS. 18 and 19. In this embodiment, a compressed tablet 400 with a depressed region 401 is used as a substrate for the coating layers. A substrate such as a similarly shaped lozenge or a gum could also be used. The substrate can alternatively be porous which allows the deposited liquid material to penetrate a distance into the core of the tablet through capillary action. The construction of the dosage form starts with the application of a first layer of solvent containing or a hot melt coating material 402 such as erythritol to the surface of the compressed tablet 400 using an intermediate applicator 403 with optional volumetric spacing features 404. This first coating is allowed to cool and solidify, or in the case a solvent containing material, the solidification occurs after removal of the solvent. The intermediate applicator 403 contains a fluid passage 406 for heating fluid to enable precise temperature control of the intermediate applicator 403 to keep hot melt or gelling materials in a flowable state above their melting point. In a preferred embodiment, the intermediate applicator 403 has a tip geometry that conforms to the shape of the depressed region 401 of the tablet 400. This enables a uniform coating thickness across the tablet surface. An applicator with a non-conformal geometry can alternatively be used to create a coating of varying thickness. The first coating step is illustrated in FIG. 20.

Figure 21:
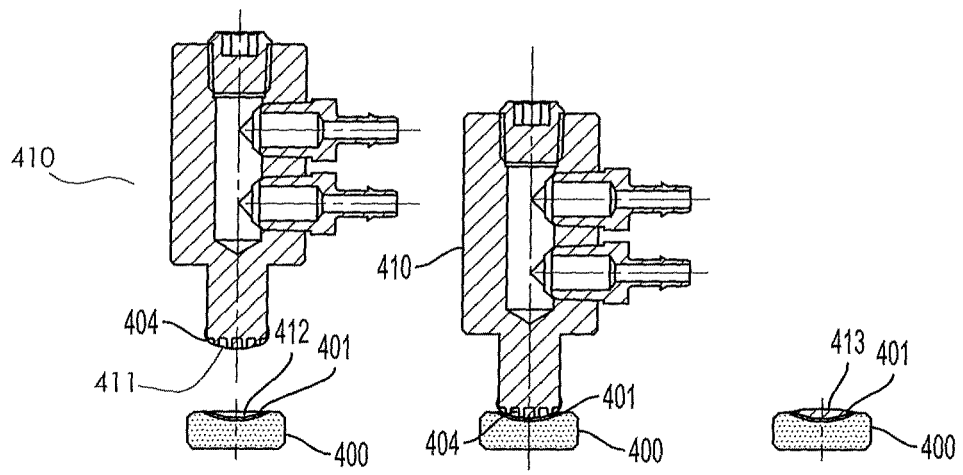

FIG. 21 illustrates the second application of the liquid fill material. Intermediate applicator 410 with optional volumetric spacing features 404 deposits the liquid fill material 411 into the coated depressed surface 412 of the compressed tablet 400. After removal of the intermediate applicator 410 the liquid fill deposit 413 remains in the recessed depression 401.

Figure 22:
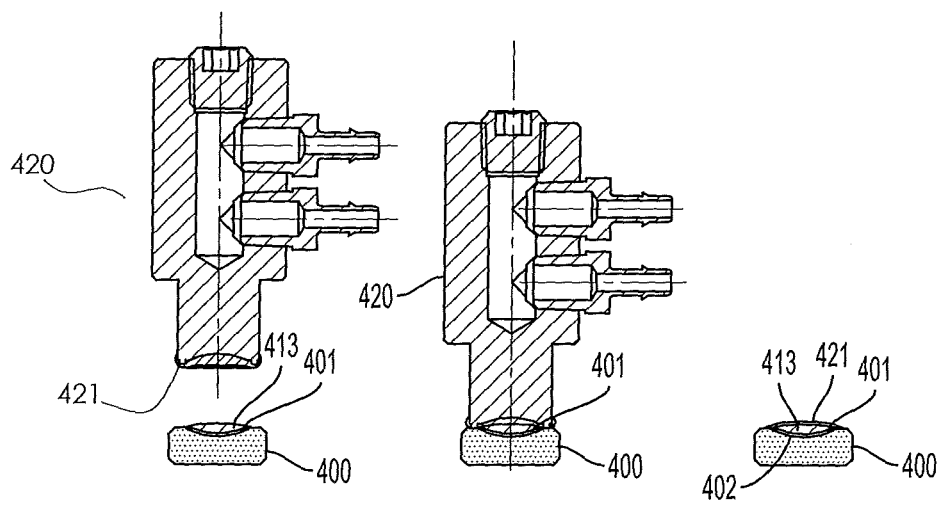
Figure 23:
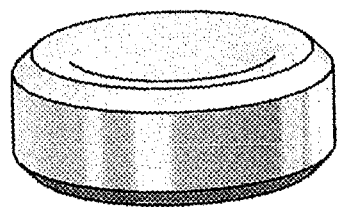
Figure 24:
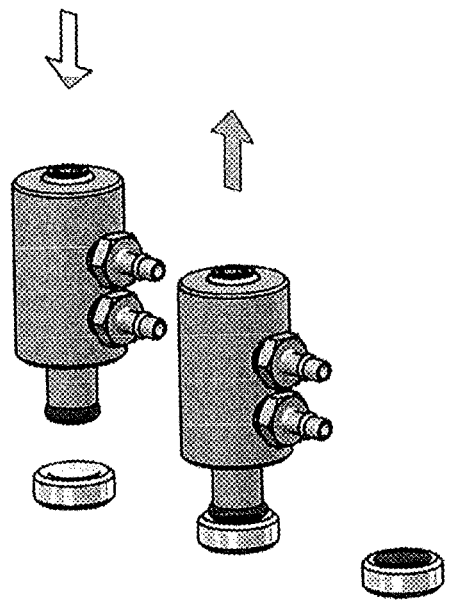
Figure 25:
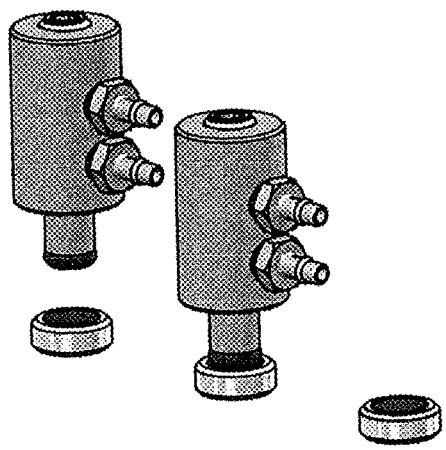
Figure 26:
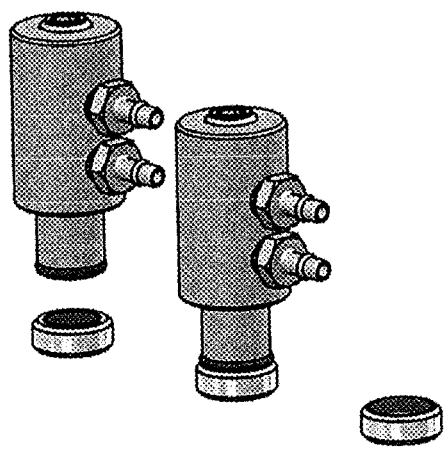
Figure 27:
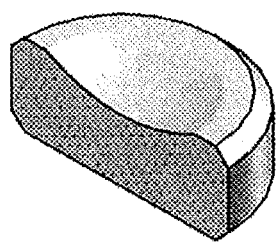
Figure 28:
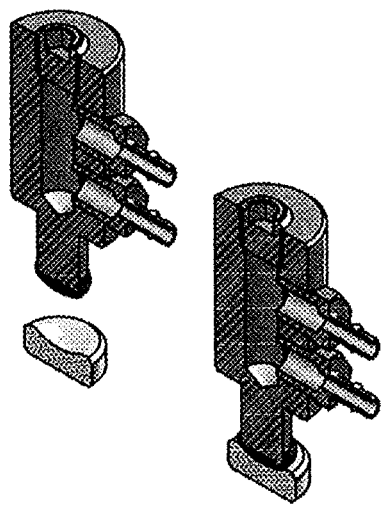
Figure 29:
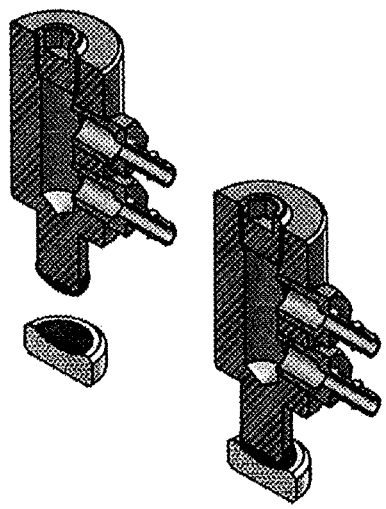
Figure 30:
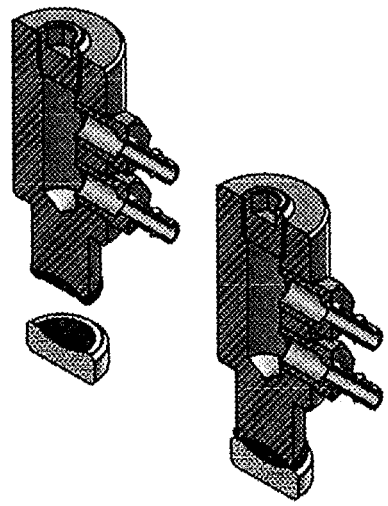

FIG. 22 illustrates the final encapsulation layer application. Intermediate applicator 420 deposits encapsulation material 421 over the surface of the previously applied liquid fill 413. The diameter (or surface area for non-circular geometries) of the intermediate applicator tip is greater than the diameter of the liquid fill deposit 413 such that the overlap can create a perimeter seal around the liquid fill material.

FIGS. 23 through 26 illustrate a 3-D representation of the processes previously described.

FIGS. 27 through 30 illustrate a 3-D cross sectional view of the processes previously described.

Figure 31:
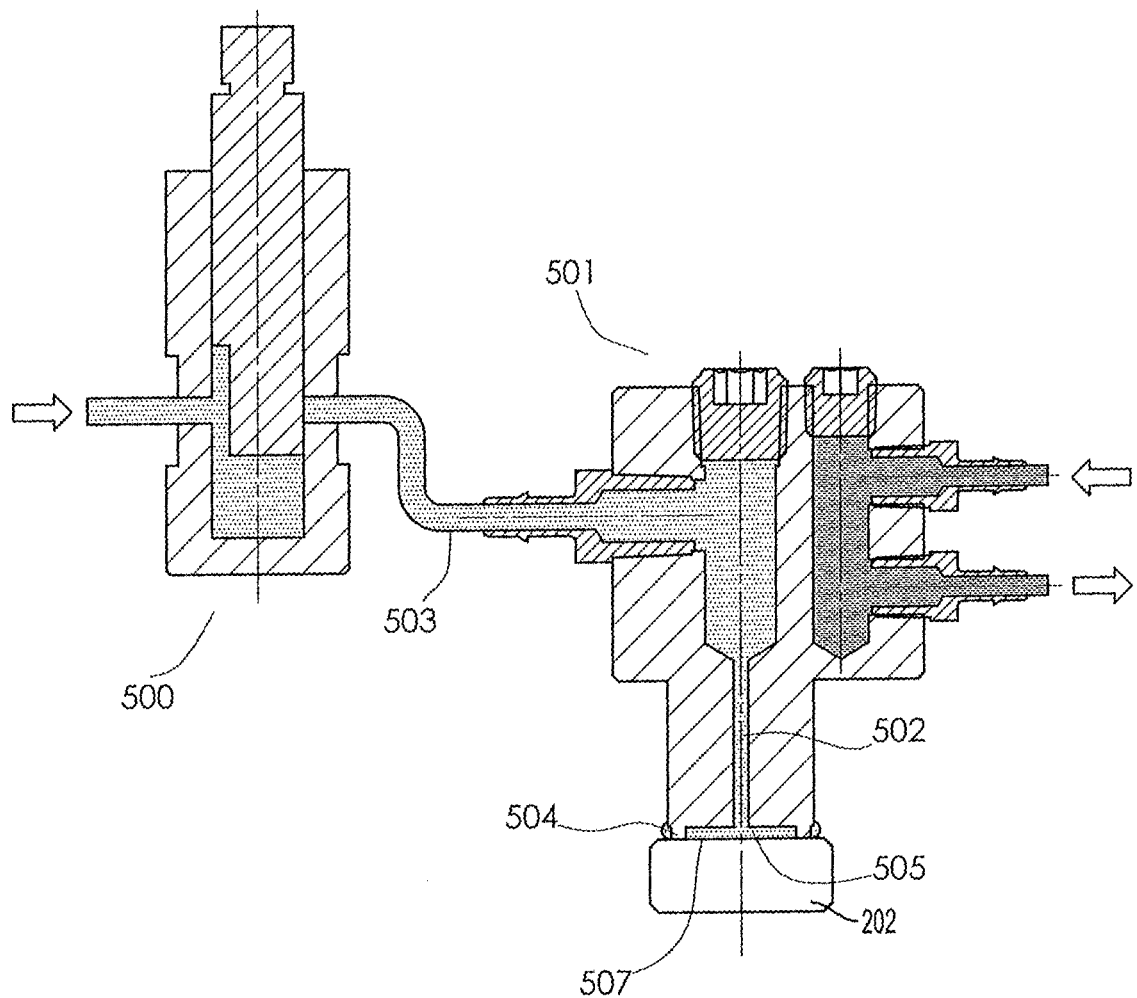

FIG. 31 illustrates an alternative embodiment where a pump 500 is used in combination with an intermediate applicator 501 to accomplish the deposition of coating material to the substrate surface. As has been previously described, the intermediate applicator 201 was charged using a fluid bath 200 (see FIG. 14). The use of the fluid bath methodology has a drawback when highly viscous materials are required as coating material due to poor flow behavior. By eliminating the fluid bath as a means of charging the applicator and substituting a precision meter pump 500 to inject coating material directly to the tip of the applicator through a fluid passageway 502, highly viscous materials can be accurately deposited. A positive displacement meter pump 500 is connected to an intermediate applicator 501 with fluid passageway 502 via tubing 503. The intermediate applicator 501 also contains volumetric spacing features 504 which set a fixed volume cavity for accurate dosing on the surface of the substrate. A preset volume of viscous coating material 505 is injected via the positive displacement meter pump 500 into the cavity 507 created by the volumetric spacing features 504 and the surface of the medicament 202. This volumetric cavity establishes the geometry and shape of the coating material on the tablet surface.

Figure 32:
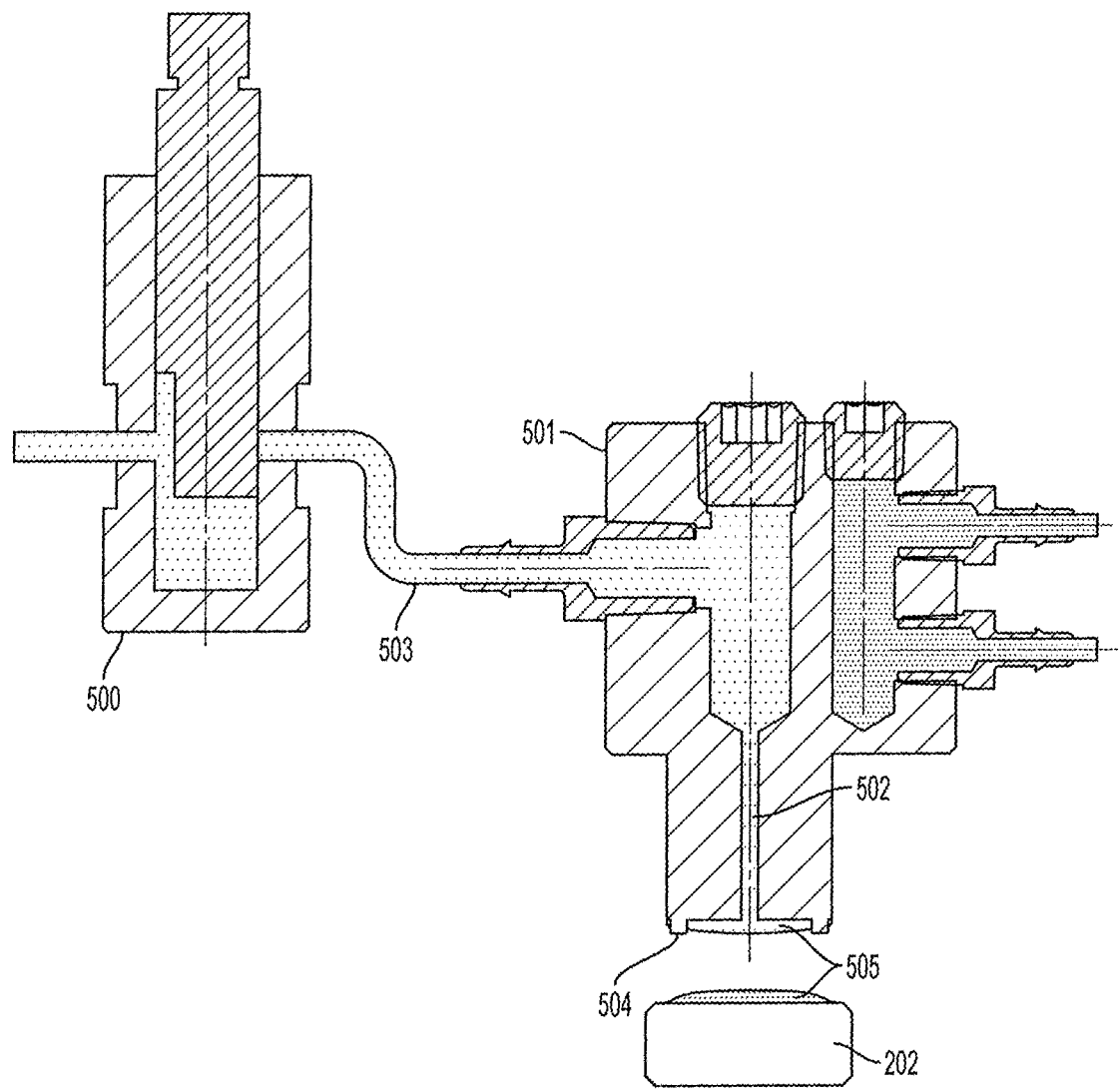

FIG. 32 illustrates the intermediate applicator 501 with fluid passageway 502 withdrawing from the surface of the substrate.

DETAILED DESCRIPTION OF INVENTION

As used herein, the term "dosage form" applies to any solid composition designed to contain a specific pre-determined amount (dose) of a certain ingredient, for example an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. In a particularly preferred embodiment, the dosage form is an orally administered system for delivering a pharmaceutical active ingredient to the gastro-intestinal tract of a human. In another preferred embodiment, the dosage form is an orally administered "placebo" system containing pharmaceutically inactive ingredients, and the dosage form is designed to have the same appearance as a particular pharmaceutically active dosage form, such as may be used for control purposes in clinical studies to test, for example, the safety and efficacy of a particular pharmaceutically active ingredient.

Figure 1:
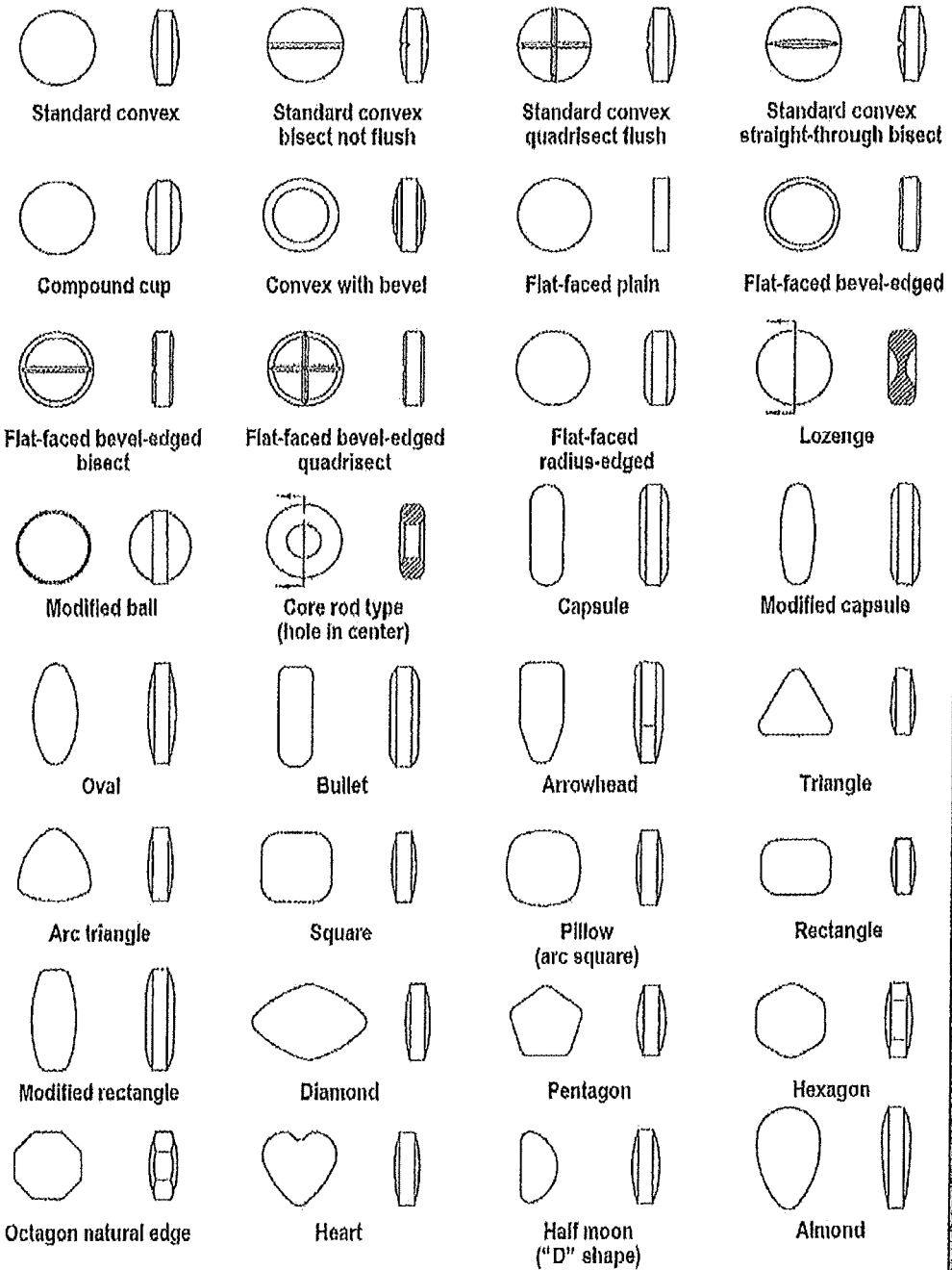
FIG. 1 is a diagram showing examples of common tablet shapes, Tablets & Capsules, November 2011, Copyright CSC Publishing.

As used herein the term "tablet" refers to a solid form prepared by compaction of powders on a tablet press, as well known in the pharmaceutical arts. Tablets can be made in a variety of shapes, including round, or elongated, such as flattened ovoid or cylindrical shapes. Examples of common tablet shapes are shown in FIG. 1. As used herein, a "caplet core" refers to one type of elongated, generally cylindrical or capsule-shaped tablet having straight or slightly bowed sides, and a generally circular cross-section, and having a length to diameter ratio from about 2 to about 5, e.g., from about 2.5 to about 3.5, say about 3.

Figure 2:
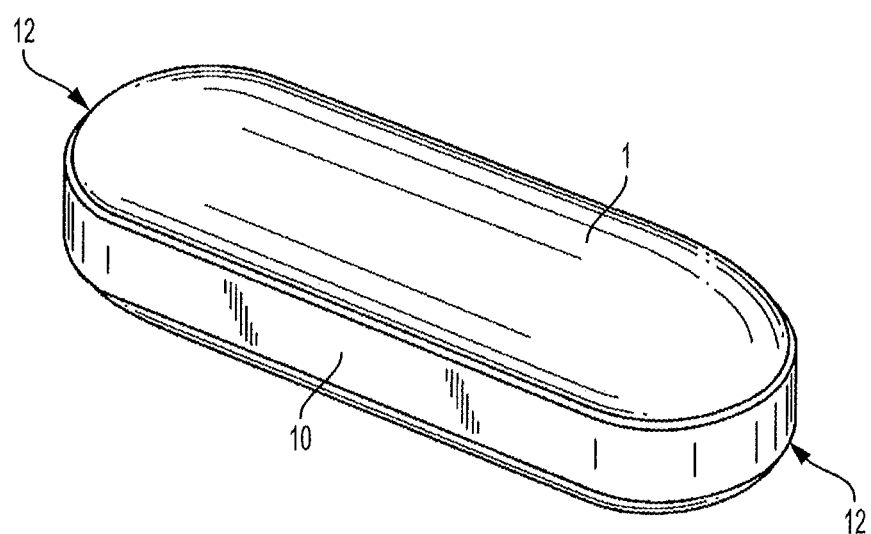
FIG. 2 is a diagram showing a standard caplet 1.
Figure 3A:
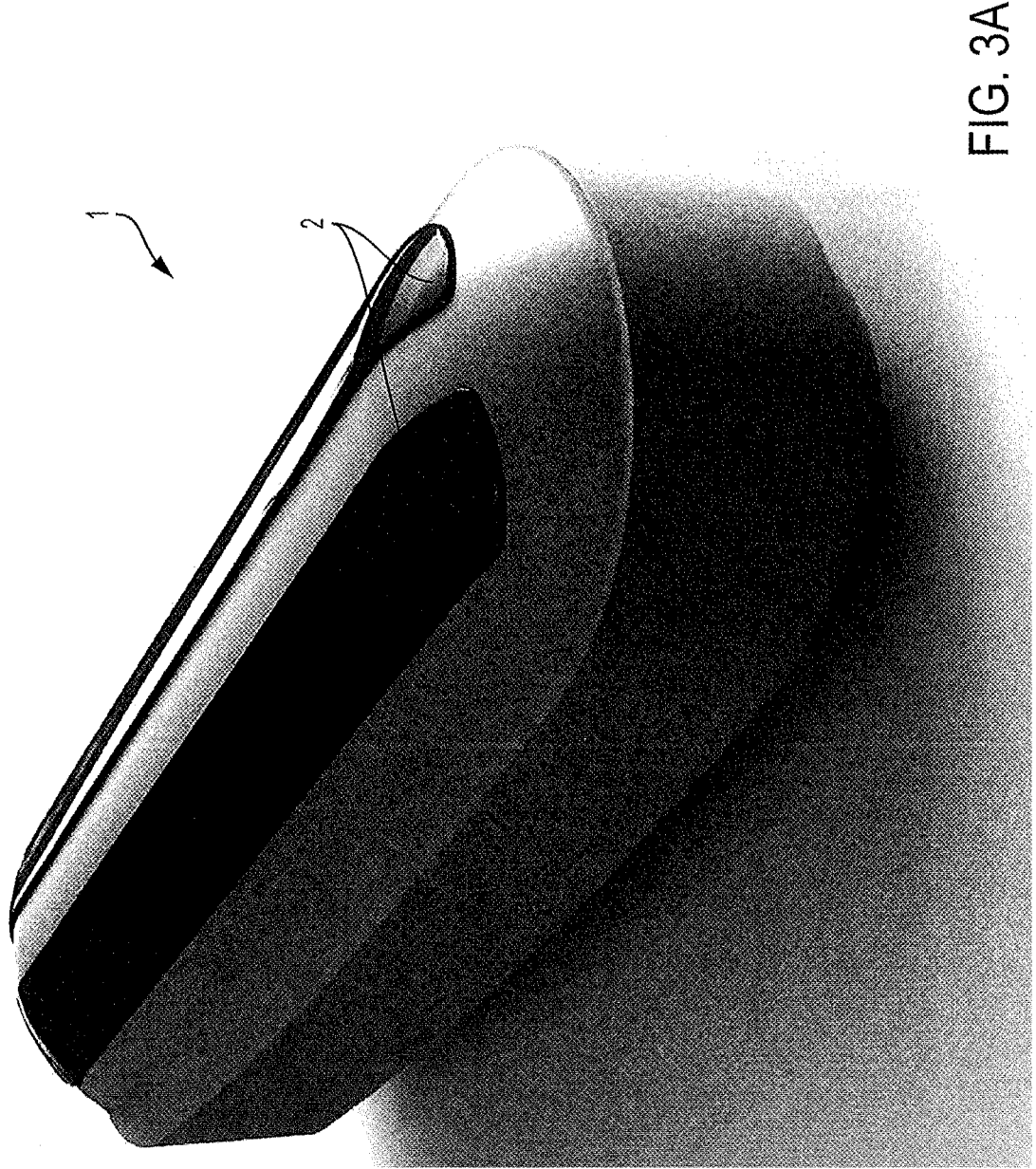
FIGS. 3A-3F are photographs showing standard caplets 1 coated with two longitudinal discontinuous coated regions 2 in accordance with an embodiment of the invention.
Figure 3B:
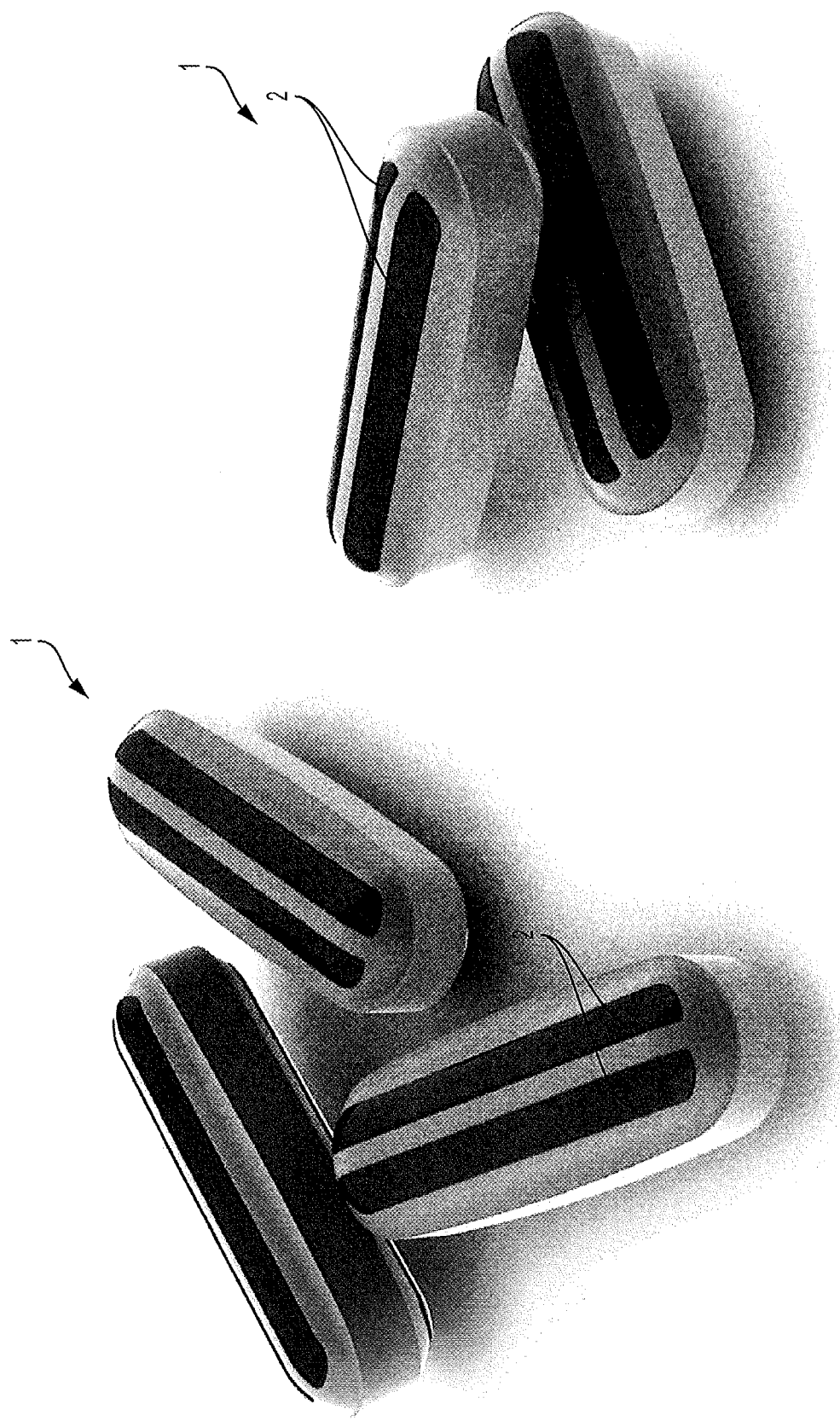
Figure 3C:
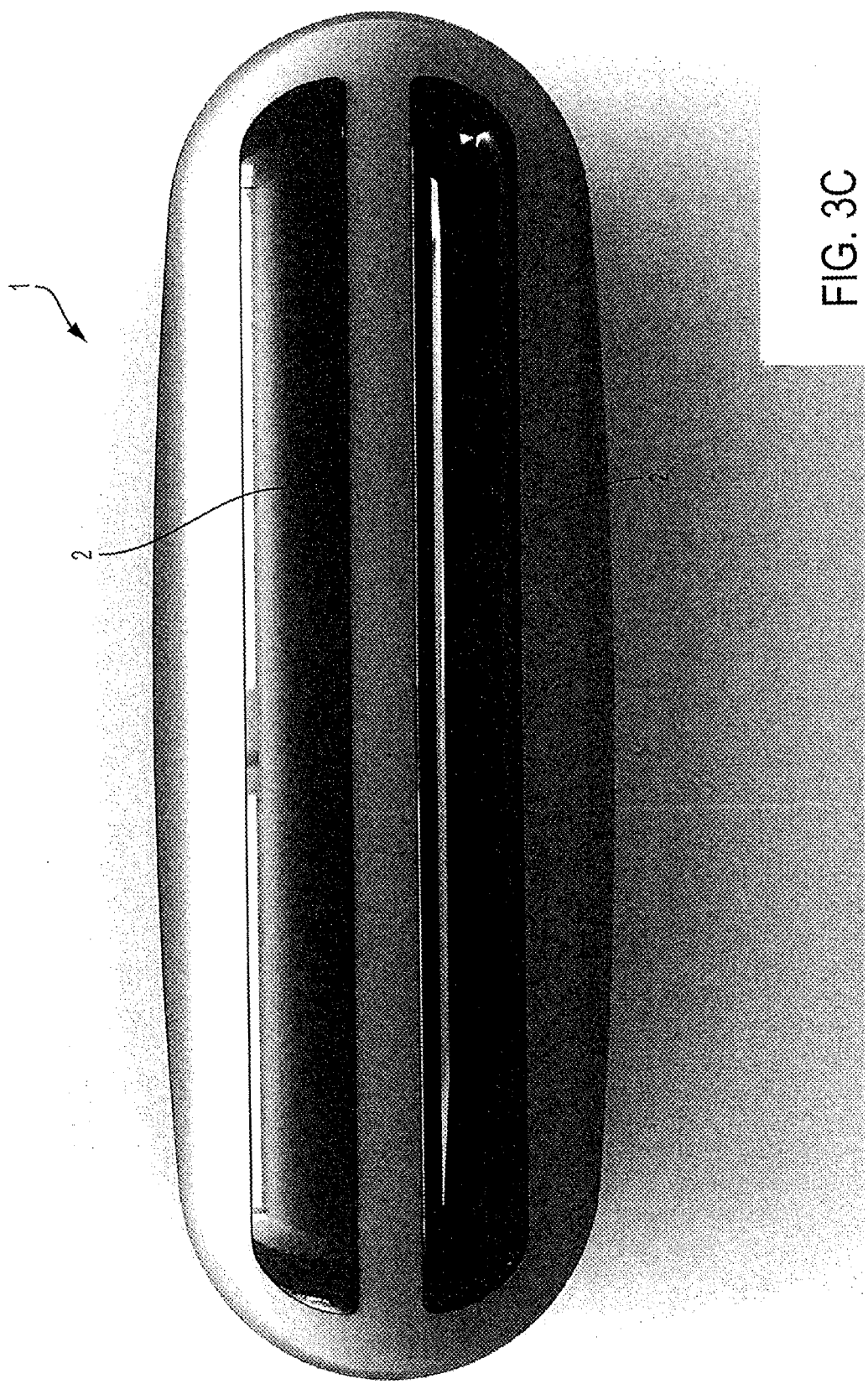
Figure 3D:
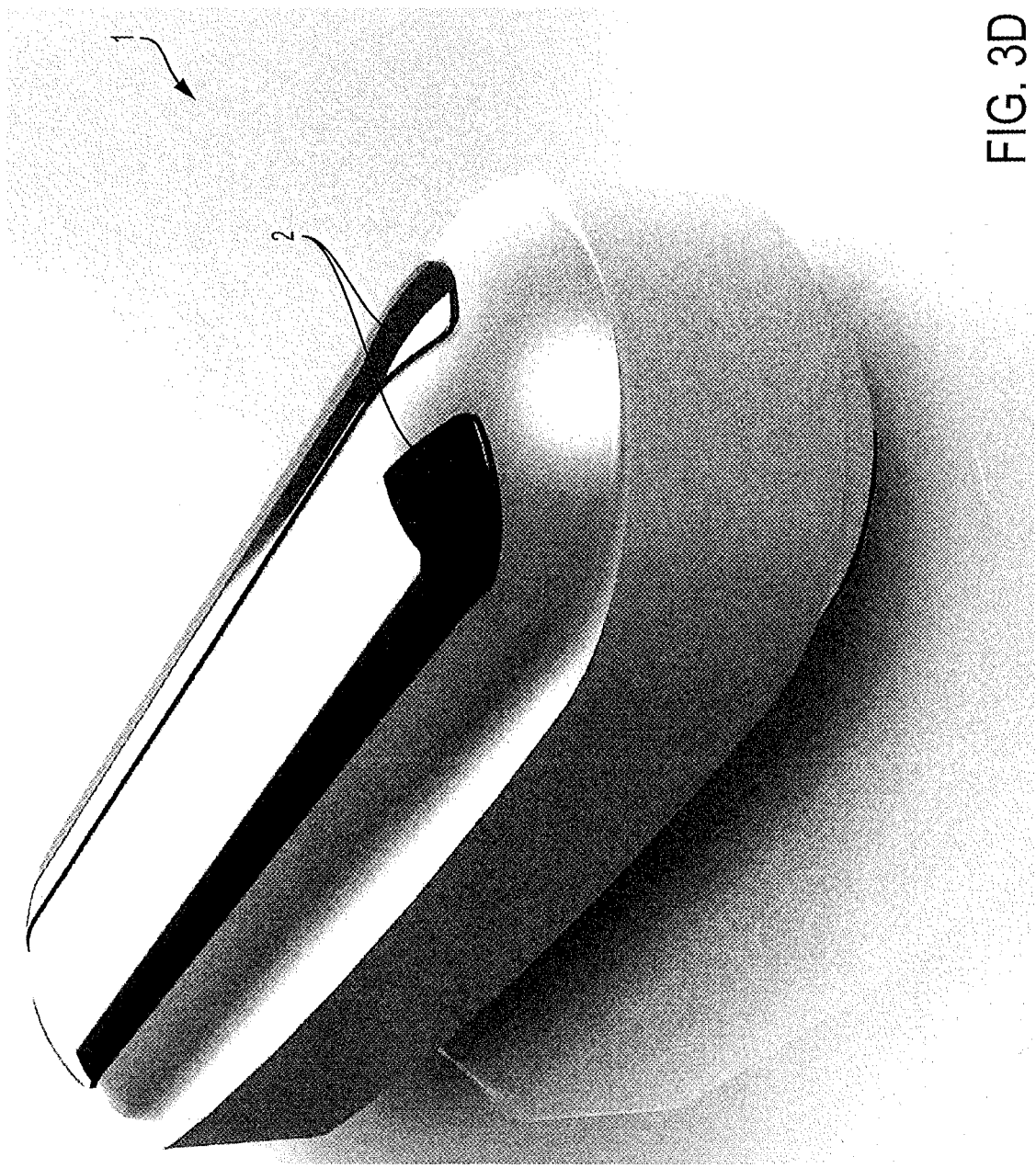
Figure 3E:
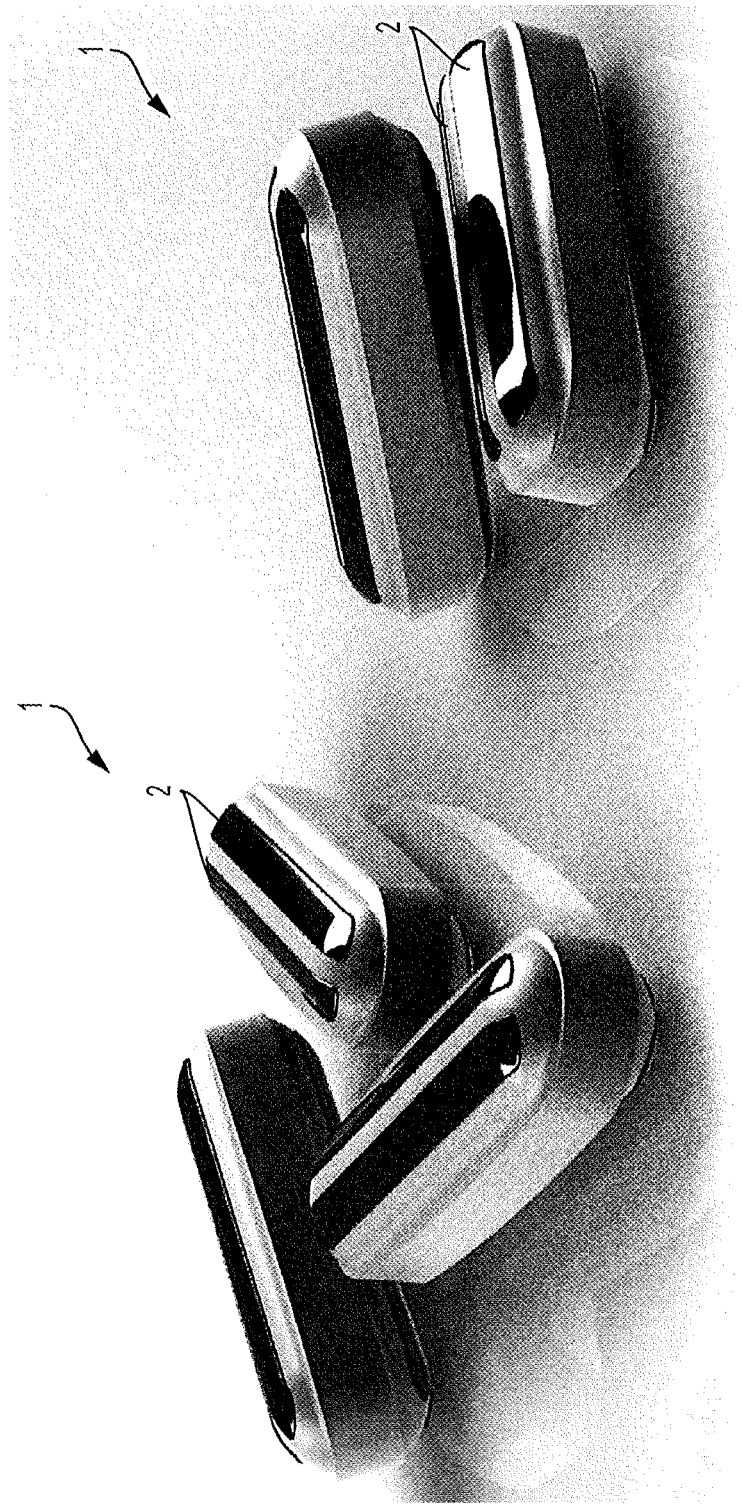
Figure 3F:
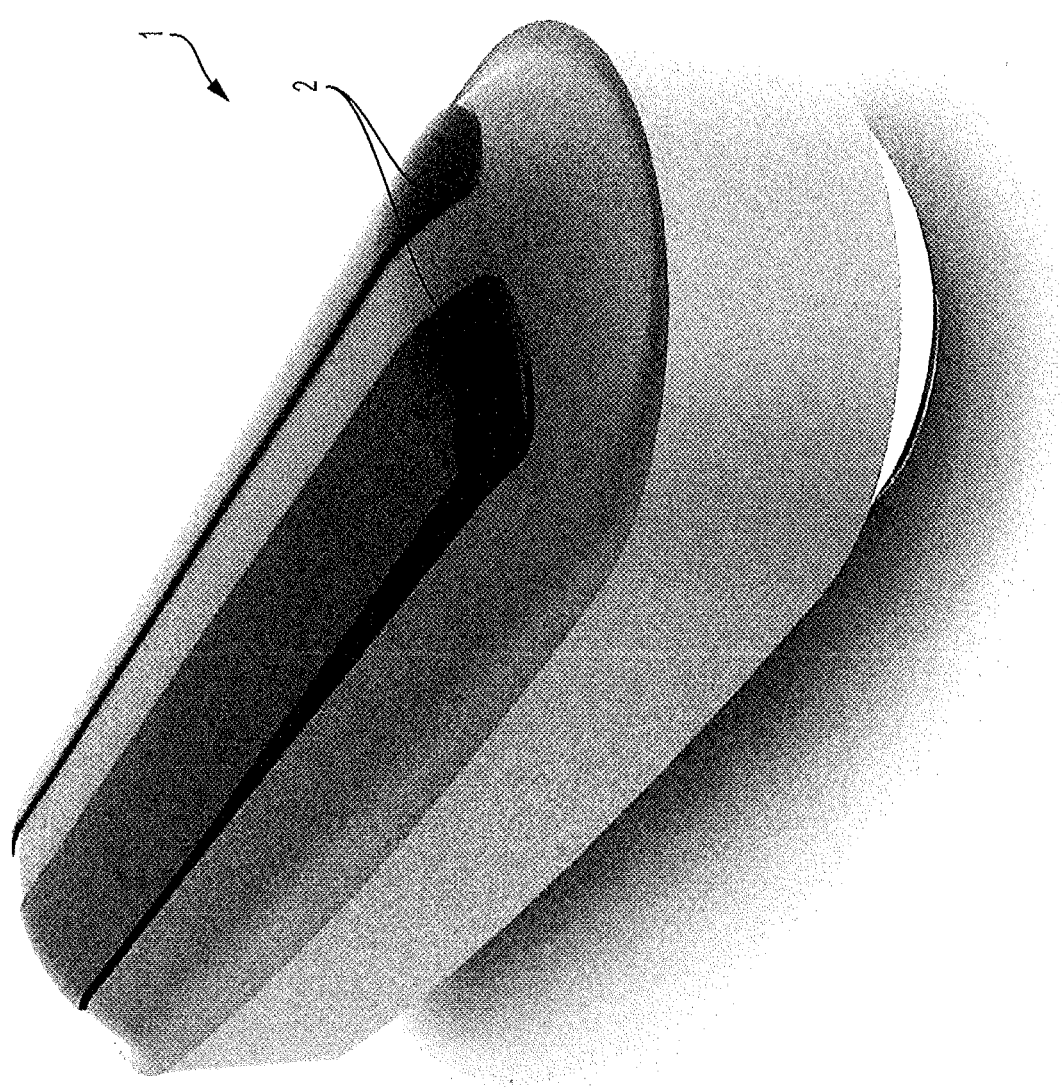
Figure 4:
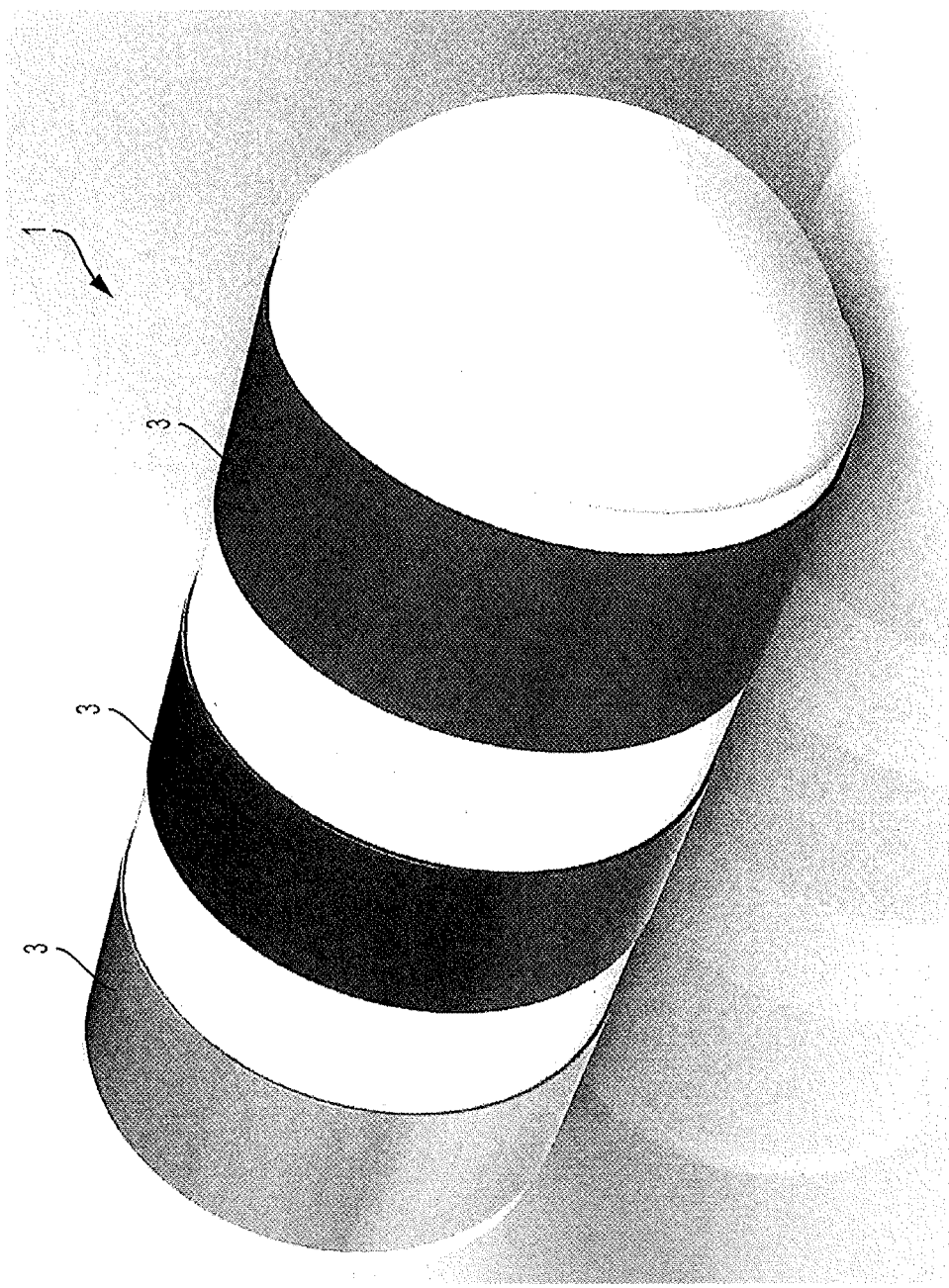
FIG. 4 is a photograph showing a standard caplet 1 coated with three circumferential discontinuous coated regions 2 in accordance with an embodiment of the invention.
Figure 5A:
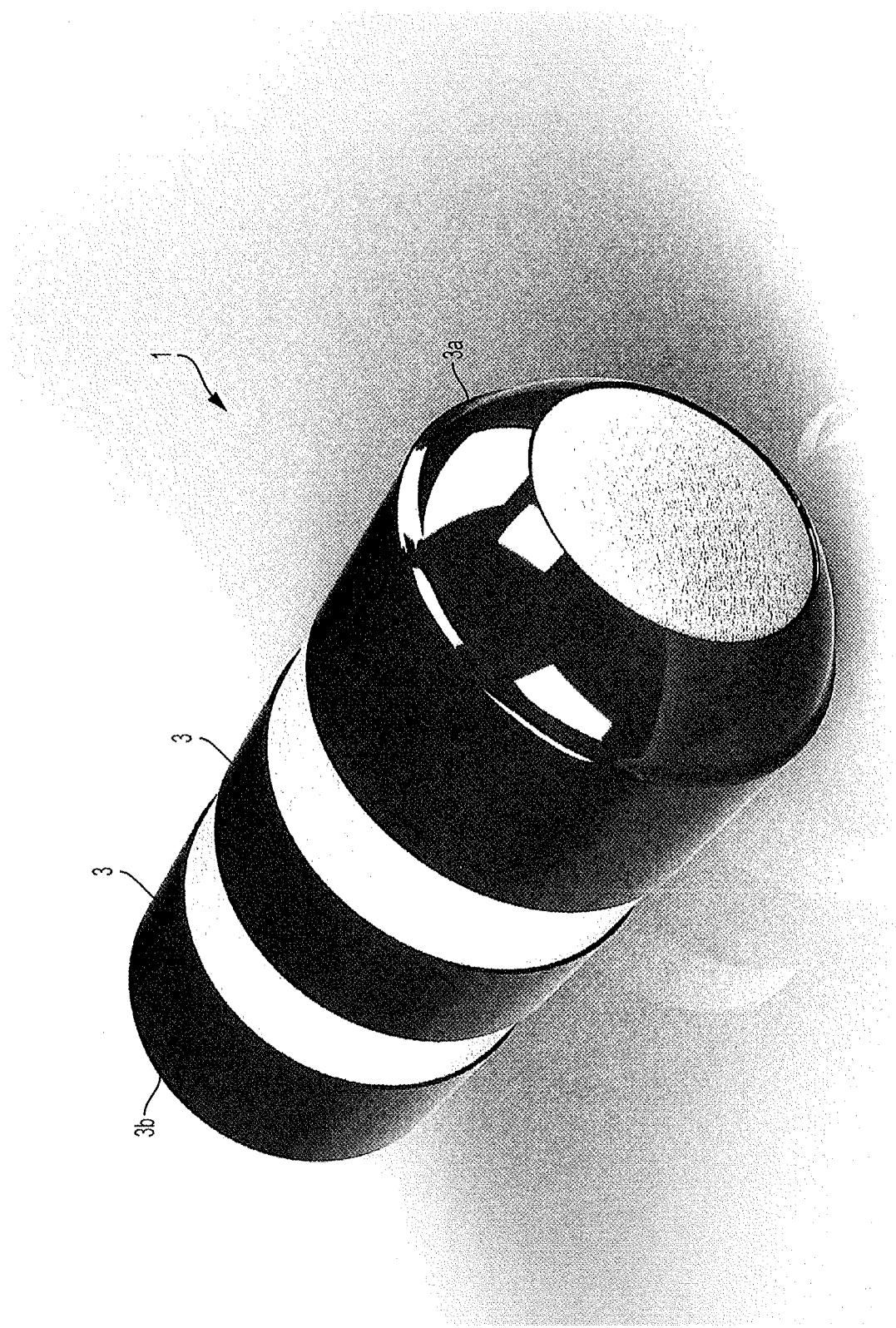
FIGS. 5A and 5B are photographs showing standard caplets 1 coated with three circumferential discontinuous coated regions 3, wherein two end circumferential discontinuous coated regions 3a and 3b each cover a portion of the end portions of the caplet, in accordance with an embodiment of the invention.
Figure 5B:
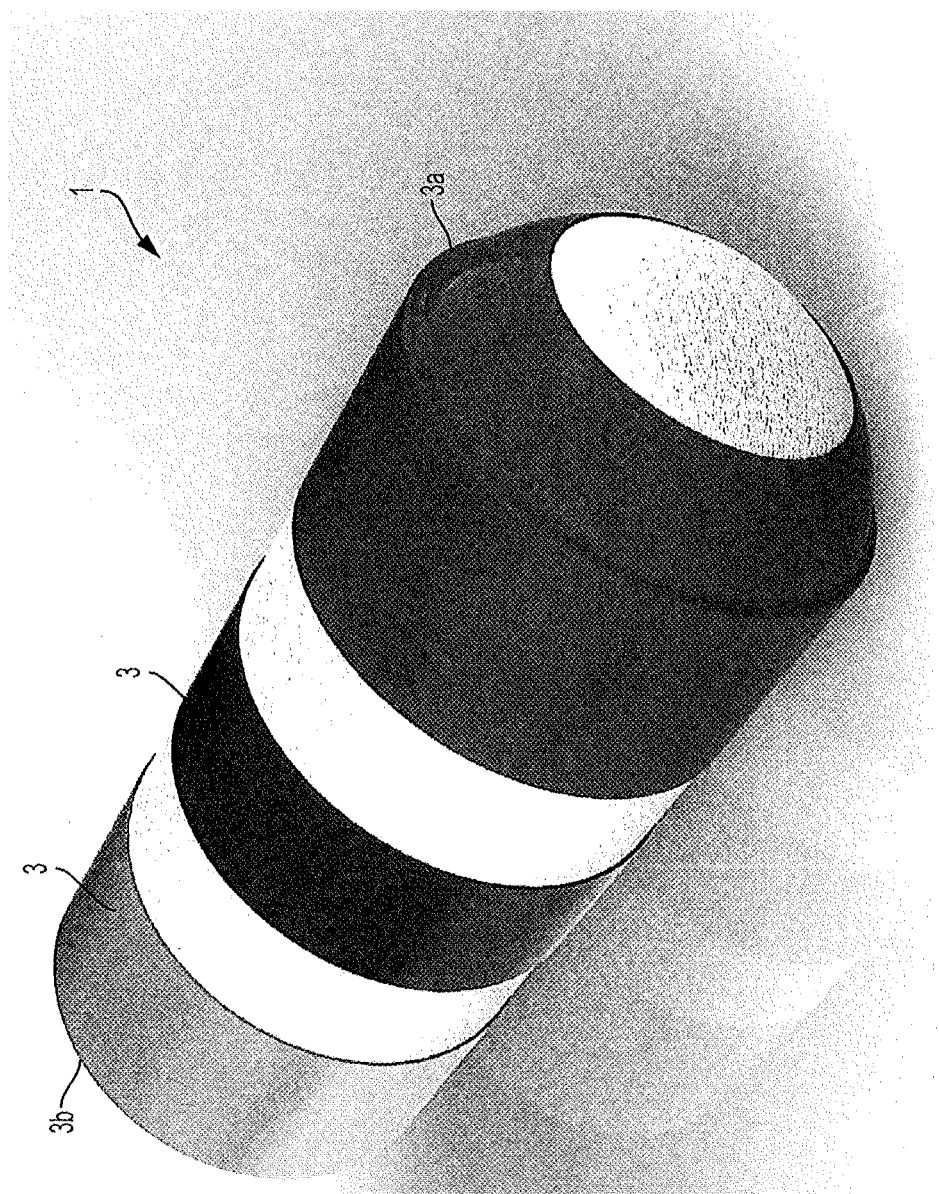
Figure 6A:
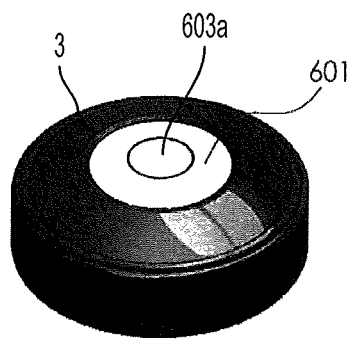
FIGS. 6A and 6B are diagrams showing a standard convex tablet 601 coated with a circumferential discontinuous coated region 3 over a substantial portion of the standard convex tablet 601, in accordance with an embodiment of the invention.
Figure 6B:
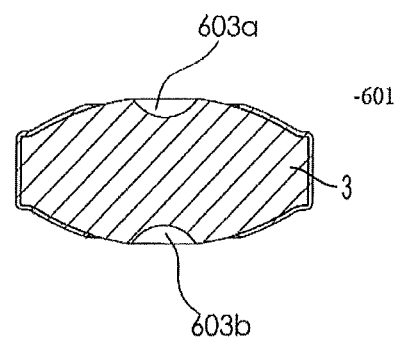
Figure 6C:
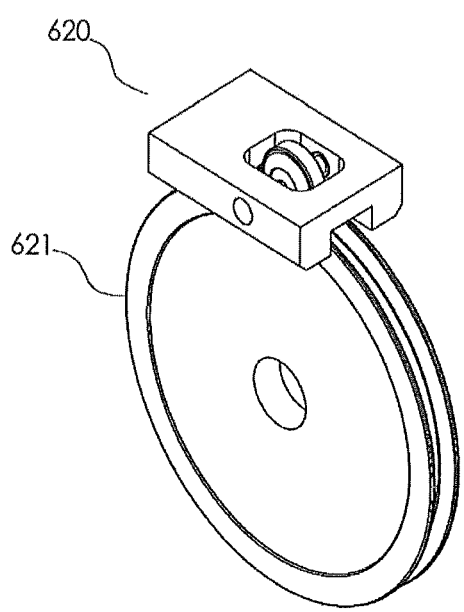
FIGS. 6C and 6D are diagrams showing apparatus that may be used to prepare the coated tablet shown in FIGS. 6A and 6B. The circumferential discontinuous coated region 3 of FIG. 6A is applied with the aid of a fixture apparatus FIG. 6C, 620 which is designed to engage depressed features FIGS. 6A and 6B, 603a and 603b, which are located on both sides of the standard convex tablet 601. The standard convex tablet 601 is thus able to rotate about the axis through the depressed features 603a and 603b enabling the circumferential coating of the standard convex tablet 601 by a conformal coating wheel FIG. 6C, 621. Any movable surface that would permit rotation and coating of the tablet is envisioned to be within the scope of the present invention.
Figure 6D:
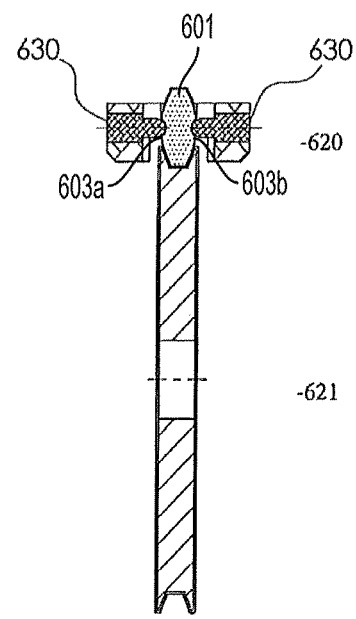
Figure 6E:
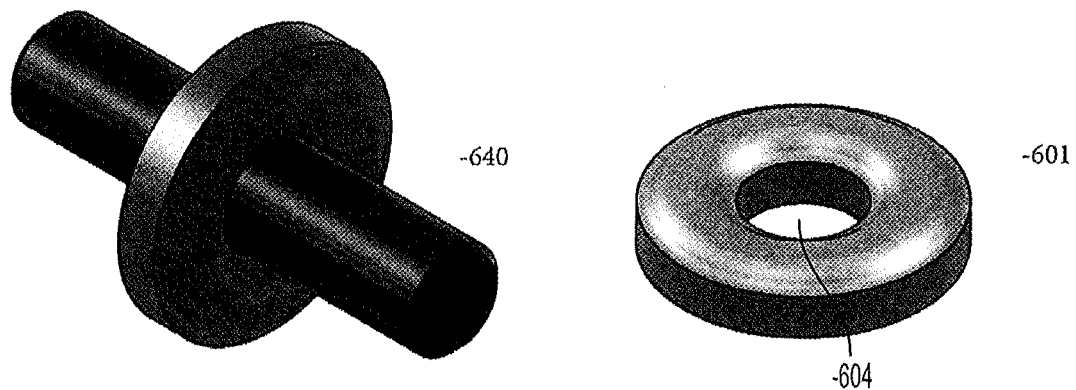
FIG. 6E is an alternate embodiment of the invention where standard convex tablet 601 has a hole 604 that can be used to enable an axis of rotation around a pin 640.
Figure 6F:
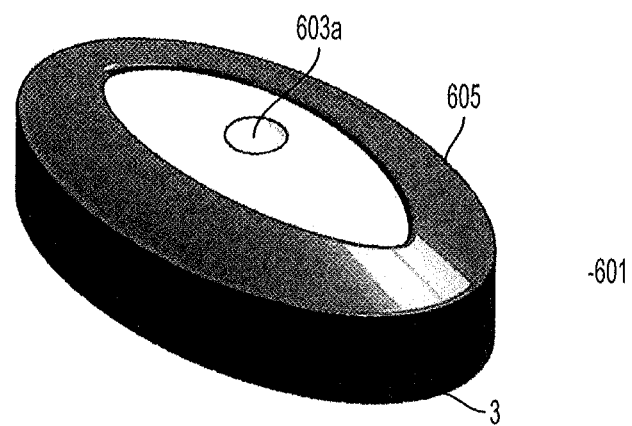
FIG. 6F is another embodiment of the invention where the standard convex tablet 601 has a non-circular perimeter 605.
Figure 6G:
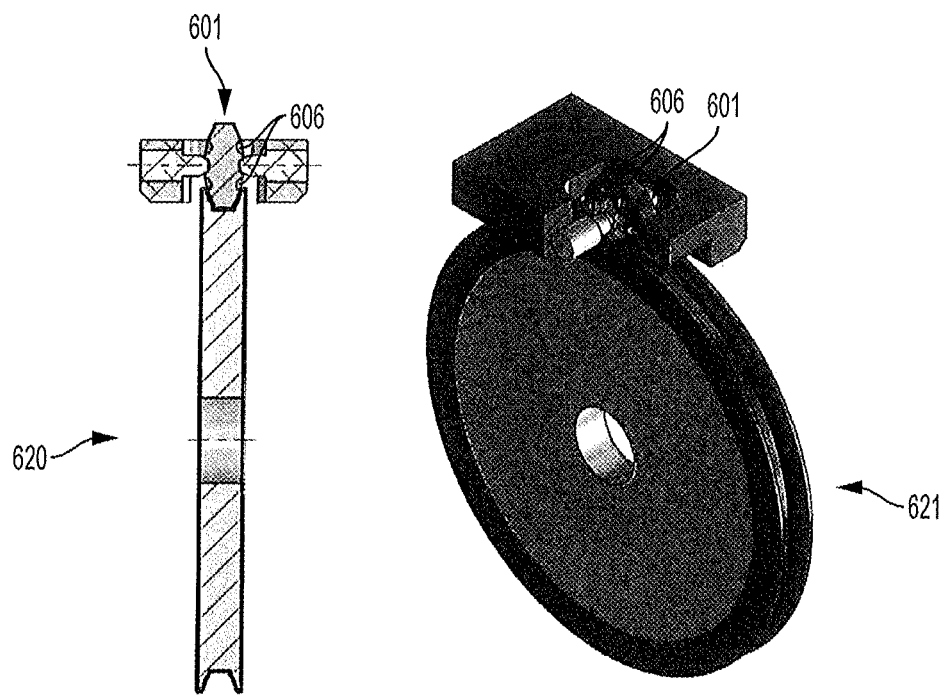
FIG. 6G is a further embodiment of the invention where depressions 606 in the standard convex tablet 601 coincide with the region of the standard convex tablet 601 covered by the conformal coating wheel 621. These depressions 606 are of sufficient depth to avoid being coated by the coating solution. The standard convex tablet 601 then has the appearance shown in FIG. 6H.
Figure 6H:
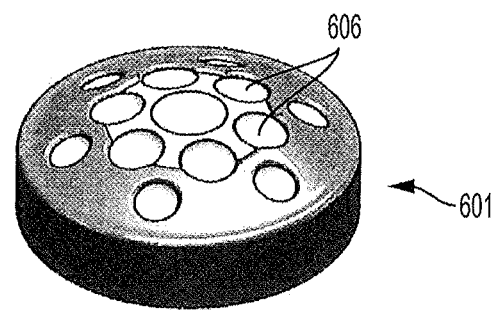
Figure 7A:
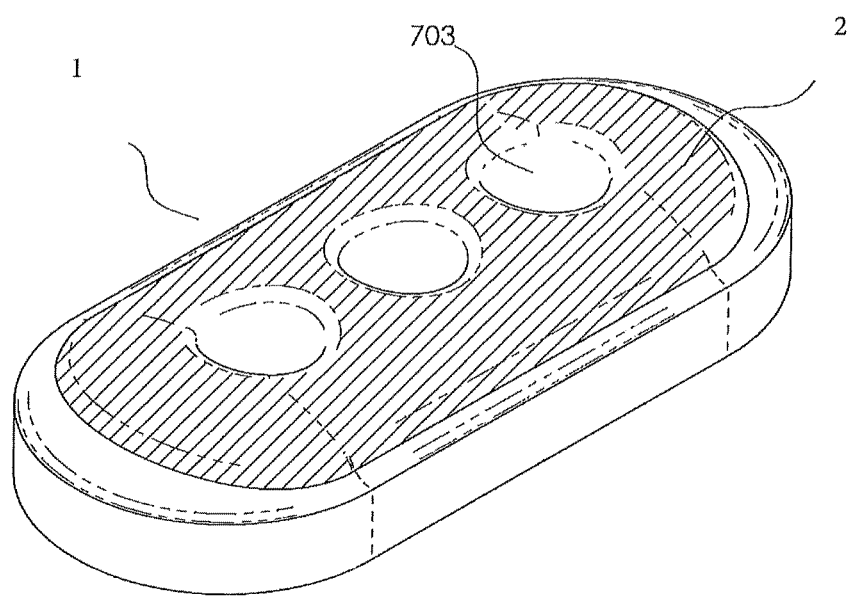
FIG. 7A is a diagram showing a standard caplet lcoated with a longitudinal discontinuous coated region 2, wherein the longitudinal discontinuous coated region 2 contains one or more openings 703, in accordance with an embodiment of the invention.
Figure 7B:
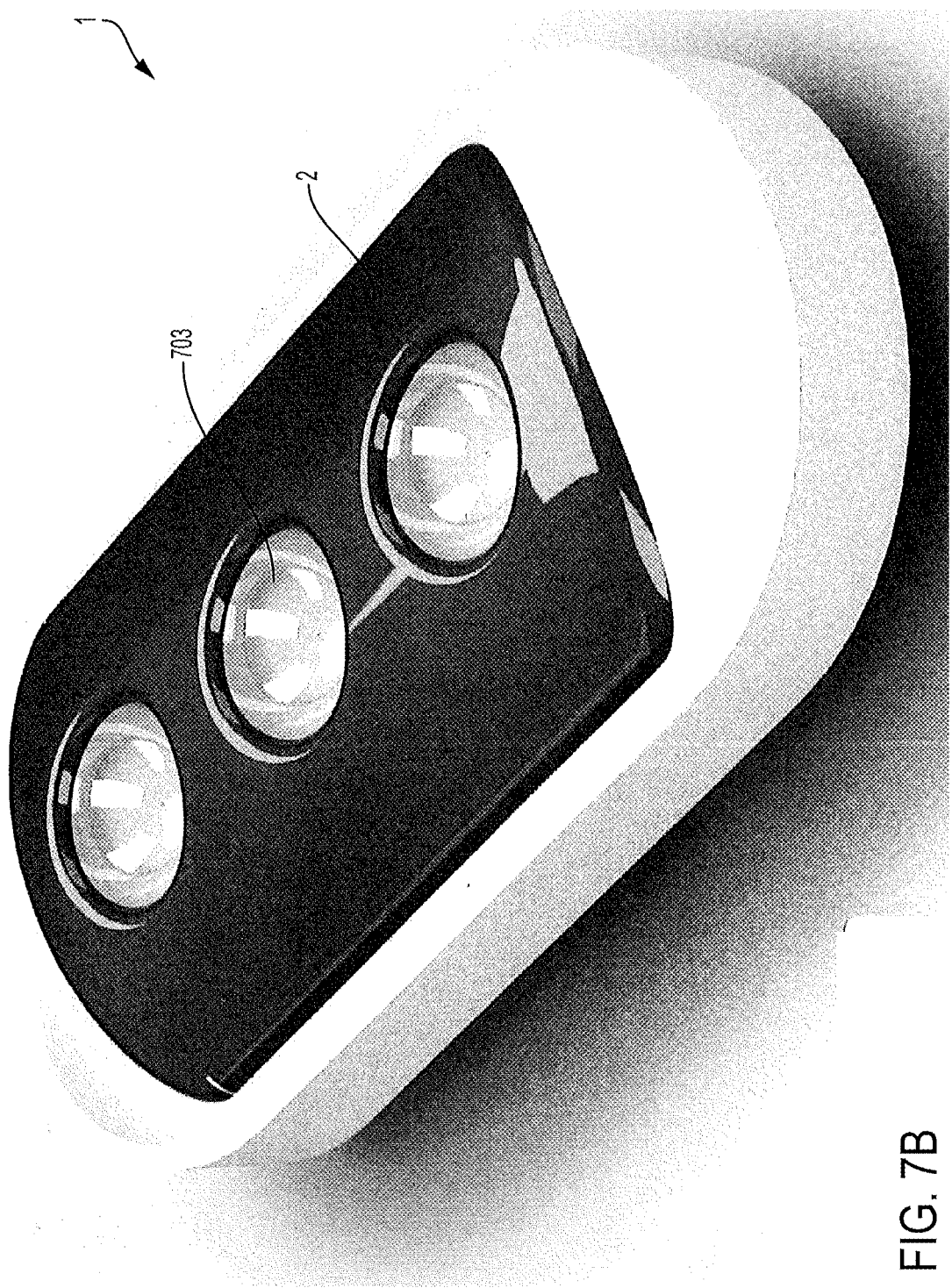
FIG. 7B is a photograph showing the dosage form of FIG. 7A.

A caplet is one type of elongated tablet covered by a film coating. An example of a standard caplet is shown in FIG. 2. Referring to FIG. 2, a core 10 in the shape of an elongated tablet has two ends 12 at opposing sides of a longitudinal axis. A bellyband 14 may occur along the longitudinal circumference where the tablet is in contact with die walls during compaction.

The core can have any number of pharmaceutically acceptable tablet shapes. Tablet is meant to encompass shaped compacted dosage forms in the broadest sense and should not be limited to the shapes shown in FIG. 1. An elongated tablet is a type of tablet having an elongated shape. One type of caplet core shown in FIG. 2 has a generally circular cross section that generally tapers from the mid-section to a tip or end region. For purposes of this application, the longitudinal axis passes through the center of both ends of the caplet core.

The core (or substrate) may be any solid form. The core may be prepared by any suitable method, for example the core be a compressed dosage form, or may be molded. As used herein, "substrate" refers to a surface or underlying support, upon which another substance resides or acts, and "core" refers to a material that is at least partially enveloped or surrounded by another material. For the purposes of the present invention, the terms may be used interchangeably: i.e., the term "core" may also be used to refer to a "substrate." Preferably, the core comprises a solid, for example, the core may be a compressed or molded tablet, hard or soft capsule, suppository, or a confectionery form such as a lozenge, nougat, caramel, fondant, or fat based composition.

Figure 8:
FIG. 8 is a diagram showing the dimensions of a standard caplet 1 coated with three circumferential discontinuous coated regions 3, wherein two end circumferential discontinuous coated regions 3*a* and 3*b* each cover a portion of the end portions of the caplet, in accordance with an embodiment of the invention.
Figure 8:
Figure 8:
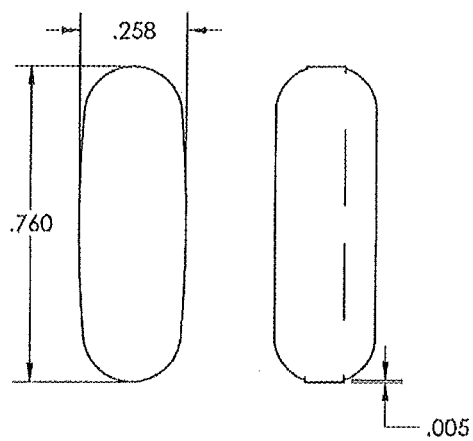
Figure 8:
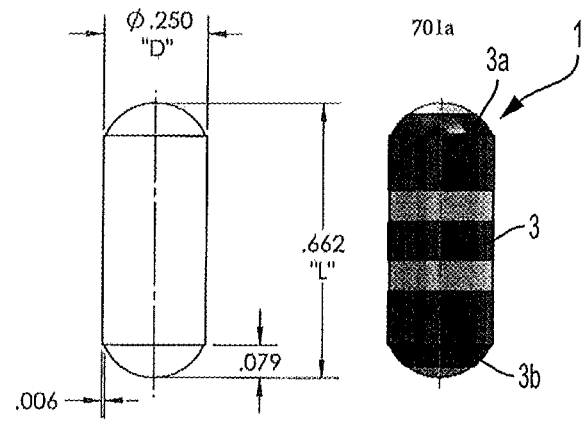
Figure 8:
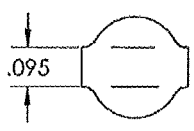
Figure 8:
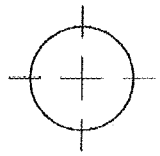
Figure 9A:
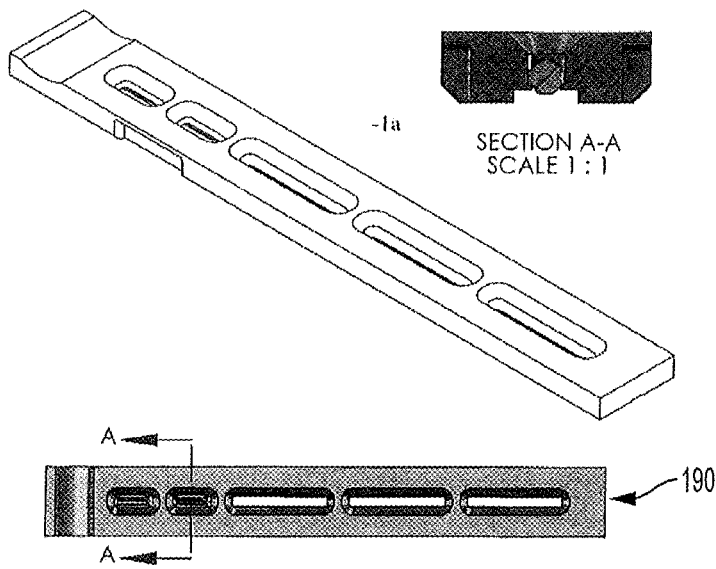
FIGS. 9A-9C are diagrams showing various carrier trays 190 that can be used to apply one or more circumferential discontinuous coated regions 3 to a dosage form in accordance with an embodiment of the invention.
Figure 9C:
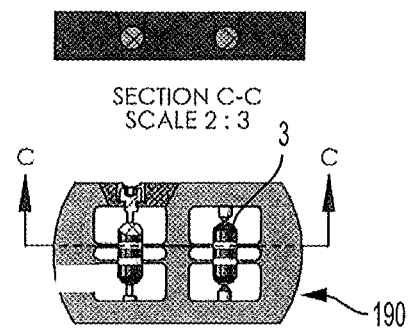
Figure 9B:
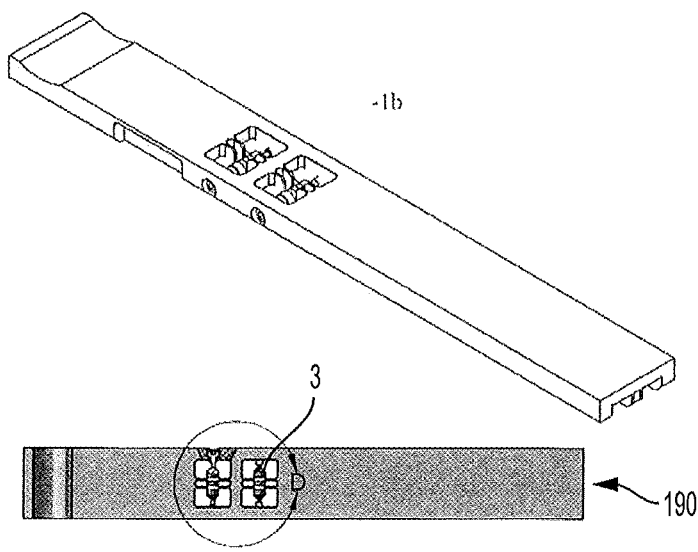

In one embodiment, the core has one or more major faces. The core may be in a variety of different shapes. For example, in one embodiment the core may be in the shape of a truncated cone. In other embodiments the core may be shaped as a polyhedron, such as a cube, pyramid, prism, or the like; or may have the geometry of a space figure with some non-flat faces, such as a cone, cylinder, or the like. Exemplary core shapes that may be employed include tablet shapes formed from compression tooling shapes described by "The Elizabeth Companies Tablet Design Training Manual" (Elizabeth Carbide Die Co., Inc., p. 7 (McKeesport, Pa.)) (incorporated herein by reference) as follows (the tablet shape corresponds inversely to the shape of the compression tooling):

Shallow Concave.
Standard Concave.
Deep Concave.
Extra Deep Concave.
Modified Ball Concave.
Standard Concave Bisect.
Standard Concave Double Bisect.
Standard Concave European Bisect.
Standard Concave Partial Bisect.
Double Radius.
Bevel & Concave.
Flat Plain.
Flat-Faced-Beveled Edge (F.F.B.E.).
F.F.B.E. Bisect.
F.F.B.E. Double Bisect.
Ellipse.
Oval.
Capsule.
Rectangle.
Pentagon.
Octagon.
Diamond.
Arrowhead.
Bullet.
Barrel.
Half Moon.
Shield.
Heart.
Almond.
Parallelogram.
Trapezoid.
FIG. 8/Bar Bell.
Bow Tie.
Uneven Triangle.

The core may be pressed of a blend of suitable active ingredients and excipients which may be either their natural color, including white, or can be conventionally colored as desired to provide a core of any desired color.

According to an embodiment, the core may contain a disintegrant and/or a superdisintegrant. Suitable disintegrants for making the core, or a portion thereof, by compression, include, e.g., sodium starch glycolate, cross-linked polyvinylpyrrolidone, cross-linked carboxymethylcellulose, starches, microcrystalline cellulose, and the like. According to an embodiment, the superdisintegrant is present as a percentage of the weight of the core from about 0.05 percent to about 10 percent.

The dosage form of the present invention preferably contains one or more active ingredients. Suitable active ingredients broadly include, for example, pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, anti-smoking agents, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, *senna*, phenolphthalein, aloe, castor oil, ricinoleic acid, and dehydrocholic acid, and mixtures thereof; H2 receptor antagonists, such as famotidine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate, loperamide and racecadotril; glycopyrrolate; antiemetics, such as ondansetron, analgesics, such as mesalamine.

Examples of suitable polydimethylsiloxanes, which include, but are not limited to dimethicone and simethicone, as disclosed in U.S. Pat. Nos. 4,906,478, 5,275,822, and 6,103,260, the contents of each which is expressly incorporated herein by reference. As used herein, the term "simethicone" refers to the broader class of polydimethylsiloxanes, including but not limited to simethicone and dimethicone.

In one embodiment of the invention, at least one active ingredient may be selected from bisacodyl, famotidine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, at least one active ingredient is selected from analgesics, anti-inflammatories, and antipyretics, e.g., non-steroidal anti-inflammatory drugs (NSAIDs), including a) propionic acid derivatives, e.g., ibuprofen, naproxen, ketoprofen and the like; b) acetic acid derivatives, e.g., indomethacin, diclofenac, sulindac, tolmetin, and the like; c) fenamic acid derivatives, e.g., mefenamic acid, meclofenamic acid, flufenamic acid, and the like; d) biphenylcarbodylic acid derivatives, e.g., diflunisal, flufenisal, and the like; e) oxicams, e.g., piroxicam, sudoxicam, isoxicam, meloxicam, and the like; f) cyclooxygenase-2 (COX-2) selective NSAIDs; and g) pharmaceutically acceptable salts of the foregoing.

In one particular embodiment, at least one active ingredient is selected from propionic acid derivative NSAID, which are pharmaceutically acceptable analgesics/non-steroidal anti-inflammatory drugs having a free —CH(CH$_3$) COOH or —CH$_2$CH$_2$COOH or a pharmaceutically acceptable salt group, such as —CH(CH$_3$)COO—Na+ or CH$_2$CH$_2$COO—Na+, which are typically attached directly or via a carbonyl functionality to a ring system, preferably an aromatic ring system.

Examples of useful propionic acid derivatives include ibuprofen, naproxen, benoxaprofen, naproxen sodium, fenbufen, flurbiprofen, fenoprofen, fenbuprofen, ketoprofen, indoprofen, pirprofen, carpofen, oxaprofen, pranoprofen, microprofen, tioxaprofen, suprofen, alminoprofen, tiaprofenic acid, fluprofen, bucloxic acid, and pharmaceutically acceptable salts, derivatives, and combinations thereof. In one embodiment of the invention, the propionic acid derivative is selected from ibuprofen, ketoprofen, flubiprofen, and pharmaceutically acceptable salts and combinations thereof. In another embodiment, the propionic acid derivative is ibuprofen, 2-(4-isobutylphenyl) propionic acid, or a pharmaceutically acceptable salt thereof, such as the arginine, lysine, or histidine salt of ibuprofen. Other pharmaceutically acceptable salts of ibuprofen are described in U.S. Pat. Nos. 4,279,926, 4,873,231, 5,424,075 and 5,510,385, the contents of which are incorporated by reference.

In another particular embodiment of the invention, at least one active ingredient may be an analgesic selected from acetaminophen, acetyl salicylic acid, ibuprofen, naproxen, ketoprofen, flurbiprofen, diclofenac, cyclobenzaprine, meloxicam, rofecoxib, celecoxib, metamizol sodic (dypirone), caffeine, and pharmaceutically acceptable salts, esters, isomers, and mixtures thereof.

In another particular embodiment of the invention, at least one active ingredient may be selected from phenylephrine, pseudoephedrine, phenylpropanolamine, chlorpheniramine, carbinoxamine, doxylamine, dextromethorphan, diphenhydramine, astemizole, terfenadine, fexofenadine, loratadine, desloratadine, cetirizine, acetylcysteine, guaifenesin, carbocysteine, ambroxol, bromhexine, mixtures thereof and pharmaceutically acceptable salts, esters, isomers, and mixtures thereof.

In another particular embodiment, the at least one active ingredient is an NSAID and/or acetaminophen, and pharmaceutically acceptable salts thereof.

In another embodiment, the at least one active ingredient is nicotine and related salts including but not limited to nicotine tartrate. In certain embodiments, the nicotine in any form is selected from the group consisting of the free base form of nicotine, a nicotine salt, a nicotine derivative, such as a nicotine cation exchanger, a nicotine inclusion complex or nicotine in any non-covalent binding, nicotine bound to zeolites, nicotine bound to cellulose or starch micro spheres, and mixtures thereof. Numerous nicotine salts are known, and may be used, e.g., the salts presented in Table 1, and preferably monotartrate, hydrogen tartrate (also called bitartrate or bitartrate dihydrate), citrate, malate, and/or hydrochloride In one embodiment, the core contains nicotine. In another embodiment, the core contains 2-4 mg of nicotine and the applied discontinuous coating region contains 1-3 mg of additional nicotine. In another version of this embodiment, the band is applied to one face of the form, wherein the face containing the immediate release of nicotine is applied to the mucosal surface, for instance buccal surface of the oral cavity.

In one embodiment the form of the present invention includes a method delivering nicotine and/or metabolites thereof, such as cotinine, nicotine N'-oxide, nornicotine, (S)-nicotine-N-β-glucuronide and mixtures, isomers, salts and complexes thereof as well as use and production of said formulations. Nicotine and/or metabolites thereof, such as cotinine, nicotine N'-oxide, nornicotine, (S)-nicotine-N-β-glucuronide and mixtures, isomers, salts and complexes thereof in any form and/or a nicotine-mimicking compound may be included in one or several portions of the dosage form.

One embodiment of the present invention is thus to provide an efficient and effective product, as well as methods and systems to deliver for example nicotine and/or metabolites thereof, such as cotinine, nicotine N'-oxide, nornicotine, (S)-nicotine-N-β-giucuronide and mixtures, isomers, salts and complexes thereof and/or a nicotine-mimicking compound and optionally component/components for creating an organoleptic sensation to a subject so as to obtain a transmucosal uptake of nicotine and/or metabolites thereof, such as cotinine, nicotine N'-oxide, nornicotine, (S)-nicotine-N-β-glucuronide and mixtures, isomers, salts and complexes thereof in the oral cavity of the subject. Thus, the present invention provides a method for delivering for example nicotine and/or metabolites thereof, such as cotinine, nicotine N'-oxide, nornicotine, (S)-nicotine-N-β-glucuronide and mixtures, isomers, salts and complexes thereof in any form to a subject comprising administering to a subject an oral formulation containing nicotine and/or metabolites thereof, such as cotinine, nicotine N'-oxide, nornicotinc, (S)-nicotine-N-β-gllucuronide and mixtures, isomers, salts and complexes thereof in any form into the oral cavity of the subject and if needed allowing the nicotine and/or metabolites thereof, such as cotinine, nicotine N'-oxide, nornicotine, (S)-nicotine-N-β-glucuronide and mixtures, isomers, salts and complexes thereof in any form in the oral formulation to be released in the saliva in the oral cavity and absorbed into the systemic circulation of the subject as well as a method for producing said oral formulation.

In one embodiment the dosage form may also comprise a suitable system of buffering agent/s to facilitate nicotine administration. In one embodiment the buffering agent is added to the coating and the immediate release portion of nicotine is added to the discontinuous coated region. In another embodiment the buffering agent is added to one discontinuous coated region, and the immediate release nicotine portion is added to a second discontinuous coated region. In another embodiment the buffering portion is added to a discontinuous coated region and the immediate release portion of nicotine is added to the coating. Absorption of nicotine from the oral cavity to the systemic circulation is dependent on the pH of the saliva, pH of the blood plasma and the pKa of nicotine, which is about 7.8, Thus, the level and type of buffering agent/s or combination thereof will affect the pH of the saliva and hence the absorption of nicotine in a free base form, which is the form predominantly absorbed through the mucosa.

The buffering is designed so as to achieve a transient buffering of the saliva of a subject during melting, disintegration or dissolution of the oral formulation. As the change is transient, the pH will return to its normal value after a certain period of time.

The buffering agent may be but is not limited to buffering agents selected from the group consisting of carbonate (including bicarbonate or sesquicarbonate), trometamol (2-amino-2-hydroxymethyl-1,3-propanediol, and also referred to as tromethamine, tris(hydroxymethyl aminomethane and TRIS), gtycinate, different phosphate systems such as trisodium phosphate, dlsodium hydrogen phosphate; and tripotassium phosphate, dipotassium hydrogen phosphate, glycerophosphate or citrate of an alkali metal (such as potassium or sodium, or ammonium), e g trisodium and tripotassium citrate, different hydroxides, amino acids, and mixtures thereof.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors should be considered, as known in the art. Typically, the dosage form comprises at least about 1 weight percent, preferably, the dosage form comprises at least about 5 weight percent, e.g., about 20 weight percent of one or more active ingredients. In one preferred embodiment, the core comprises a total of at least about 25 weight percent (based on the weight of the core) of one or more active ingredients.

The active ingredient or ingredients may be present in the dosage form in any form. For example, one or more active ingredients may be dispersed at the molecular level, e.g., melted or dissolved, within the dosage form, or may be in the form of particles, which in turn may be coated or uncoated. If an active ingredient is in the form of particles, the particles (whether coated or uncoated) typically have an average particle size of about 1-2000 microns. In one preferred embodiment, such particles are crystals having an average particle size of about 1-300 microns. In another preferred embodiment, the particles are granules or pellets having an average particle size of about 50-2000 microns, preferably about 50-1000 microns, most preferably about 100-800 microns.

In a preferred embodiment, the dissolution characteristics of the at least one active ingredient follow an "immediate release profile". As used herein, an immediate release profile is one in which the active ingredient dissolves without substantial delay or retardation due to the dosage form. This can be contrasted with the dissolution of modified release, e.g., delayed or controlled release dosage forms known in the art. In one embodiment, the dissolution rate of the immediately released active ingredient from the dosage form of the invention is within about 20% of the dissolution rate of the active ingredient from a pure crystalline powder of said active ingredient, e.g., the time for 50%, 75%, 80%, or 90% dissolution of active ingredient from the dosage form is not more than 20% longer than the corresponding time for 50%, 75%, 80%, or 90% dissolution of active ingredient from a pure crystalline powder of said active ingredient. In another embodiment, the dissolution of the immediately released active ingredient from the dosage form of the invention meets USP specifications for immediate release tablets, gelcaps, or capsules containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing; and for acetaminophen and codeine phosphate capsules USP 24 specifies that at least 75% of the acetaminophen contained in the dosage form is dissolved within 30 minutes in 900 mL of 0.1 N Hydrochloric acid using USP Apparatus 2 (paddles) at 50 rpm; and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes. See USP 24, 2000 Version, 19-20 and 856 (1999). In yet another embodiment, the immediately released active ingredient is acetaminophen, and when tested in 37° C. water using USP Apparatus II (paddles) at 50 rpm, at least 80%, preferably at least 85%, of the acetaminophen contained in the dosage form is released therefrom within 30 minutes.

In yet another embodiment, the time for release of at least 80%, preferably at least 85%, of at least one active ingredient contained in the dosage form is released therefrom is not more than about 50%, e.g., not more than about 40% of the time specified by the dissolution method for immediate release listed in the United States New Drug Application for that particular active ingredient.

In one particularly preferred embodiment, when the immediately released active ingredient is acetaminophen, when tested in 37° C. water using USP Apparatus II (paddles) at 50 rpm, at least 80% of the acetaminophen contained in the dosage form is released therefrom within about 6 minutes, e.g., within about 5 minutes, or within about 3 minutes.

In one embodiment the tablet and coating positions can be observed using the USP Disintegration test as outlined in USP 34-NF29, Section 701. In another embodiment the tablet and coating positions can be observed by placing the tablet into water at 37° C. without agitation.

According to an embodiment, disintegration of the tablet without agitation can be observed at less than about 30 seconds, e.g., less than about 15 seconds, e.g., less than about 10 seconds, e.g., less than about 5 seconds.

In certain preferred embodiments, the core is covered with a coating that can be any number of medicinally acceptable coverings. The use of coatings is well known in the art and disclosed in, for example, U.S. Pat. No. 5,234,099, which is incorporated by reference herein. Any composition suitable for film-coating a tablet may be used as a coating according to the present invention. Examples of suitable coatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Suitable compositions for use as coatings include those manufactured by Colorcon, a division of Berwind Pharmaceutical Services, Inc., 415 Moyer Blvd., West Point, Pa. 19486 under the tradename "OPADRY®" (a dry concentrate comprising film forming polymer and optionally plasticizer, colorant, and other useful excipients). Additional suitable coatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as Polysorbate-80, sodium lauryl sulfate and dioctyl-sodium sulfosuccinate; polycarbohydrates, pigments, opacifiers.

Preferred coatings include water soluble polymers selected from the group consisting of hydroxypropylmethyl cellulose, hydroxypropyl cellulose, methyl cellulose, polymethacrylates, polyvinyl alcohol, polyvinyl alcohol: polyethylene glycol copolymers and mixtures thereof.

According to an embodiment, the average thickness of the coating is preferably in the range from about 1 to about 150 microns, or from about 50 to about 90 microns, or from about 10 to about 90 microns, or from about 20 to about 80 microns, or from about 30 to about 70 microns.

In one embodiment, the coating comprises from about 10 percent to about 50 percent, e.g., from about 15 percent to about 20 percent of HPMC. The dried coating typically is present in an amount, based upon the dry weight of the core, from above about 0 percent to about 5 percent, or from about 1 percent to about 4 percent, or from about 2 percent to about 3 percent, or from about 1 to about 2 percent. The coating composition is optionally tinted or colored with colorants such as pigments, dyes and mixtures thereof.

In one embodiment, a layer of coating is applied to the entire exterior surface of core prior to application of one or more discontinuous coated regions. Coating can be applied as a clear, transparent coating such that the core can be seen. The choice is dictated by the preference of the manufacturer and the economics of the product. In a preferred embodiment, a commercially available pigment is included the coating composition in sufficient amounts to provide an opaque film having a visibly distinguishable color relative to the core.

The discontinuous coated regioned tablet of the invention provides an observable means of differentiation. The term "observable" (and forms thereof such as "observably," "observing," etc.) is intended to have its common meaning, i.e., perceptible (or "perceptibly," perceiving," etc. as appropriate) using any one or more of the five human senses, e.g., sight, sound, touch, taste and smell. The discontinuous coated regioned tablet described herein can employ interaction with one or more of the five senses, and particularly may employ visual, audible and tactile interaction or combinations thereof. Preferably, the discontinuous coated regioned tablet employs interaction with the visual sense.

The discontinuous coated regioned tablet of the invention can provide a mechanism by which consumers are provided with criteria that are relevant to appropriate selection or deselection of a given product. For example, the discontinuous coated regioned tablet is presented to the consumer and the consumer simply visually observes decision criteria and selects or deselects a product based on the criteria. Any type of design which functions as a cue as described herein is encompassed by the instant invention.

The "criteria" will have relevance to the decision-making process for deciding whether or not a product is appropriate for, and therefore could be purchased and used by, a consumer considering using the product. Since different criteria for use will apply to different products, the criteria will vary depending on the product being marketed. Examples of criteria include but are not limited to drug, location of symptoms, symptoms treated, time of day for use, drowsy/non-drowsy, form, flavor and combinations thereof.

Criteria as used herein includes both single (i.e., criterion) and multiple (i.e., criteria) characteristics on which a decision may be based. Therefore, criteria may include single or multiple characteristics which are relevant to the decision making process.

Each of the selectable responses will be either positively associated with appropriate purchase and use of the product by a consumer (i.e., a positive selectable response), or negatively associated with appropriate use (i.e., a negative selectable response) and therefore would be associated with deselection of the product.

The term "selection indicia" is intended to mean any observable symbol which is either positively associated with appropriate purchase and use of the product, i.e., positive selection indicia, or negatively associated with appropriate purchase and use of the product, i.e., negative selection indicia. Selection indicia include observable symbols such as graphic symbols including color coding, alphanumeric graphics, pictorial graphics and the like, and sounds such as musical notes, bells, audible language and the like, and combinations thereof. The selection indicia are chosen to be compatible with the design of the discontinuous coated regioned tablet.

For the sake of brevity, the term "indicia" as used herein includes both single symbols (i.e., indicium), such as a single color or graphic, and combinations of symbols (i.e., indicia), such as stripes of alternating colors or a specific color background with a pictorial and/or alphanumeric graphic in the foreground, and the like. Therefore, a single selection indicia may be comprised of one symbol or a combination of symbols which, when observed together as a whole, serve as a single positive or negative selection indicia.

In one embodiment the dosage form of the present invention is a multilayer tablet, e.g., a trilayer tablet or a bilayer tablet. In a further embodiment the bilayer tablet comprises a modified or sustained release layer and an immediate release layer.

In one embodiment, the discontinuous coated region is comprised of a material that is melted and solidifies upon application of the discontinuous coated region. In this embodiment, the discontinuous coated region may cool and harden at room temperature or upon cooling at a temperature less than 25° C. Suitable low-melting hydrophobic materials include polymers, meltable carbohydrates, fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, GLYCOWAX-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

Suitable meltable polymers include polyethylene oxide, polyvinyl acetate and polycapralactone.

In one embodiment, the discontinuous coated region may contain a carbohydrate which melts and flows below 200° C., preferably below 150° C., e.g., "meltable". Suitable meltable carbohydrates include polysaccharides such as polyfructose, polydextrose, inulin, hydrogen starch hydrosylate; isomalt or sugar alcohols such as xylitol, sorbitol erythritol and mixtures thereof.

In one embodiment, the discontinuous coated region is applied as a solvent based solution, and the solvent is subsequently dried off after application to the dosage form. The solvent may comprise ethanol, isopropyl alcohol or acetone. In another embodiment the solution comprises a hydro-alcoholic system, combining alcohol with water. The solution can comprise the polymer, carbohydrate, plasticizer, wax, active ingredient and mixtures thereof.

In another embodiment the discontinuous coated region comprises a gelling material, or a material that solidifies into a gel upon deposition. The discontinuous coated region is then dried after deposition to remove the water, solvent or combination of both. Suitable gelling materials may include gelatin, pectin, gellan gum, carrageenan, and xanthan gum. Suitable water soluble film forming polymers for use in the discontinuous coated region include but are not limited to hydroxypropyl cellulose, hypromellose, methylcellulose, pullulan, modified starches, and hydroxyethylcellulose.

One preferred process of manufacturing intermediate dosage form begins by compressing or compacting a tablet core into the desired shape of the medicament. As used herein, "compact, compacting, or compacted" and "compress, compressing, or compressed" may be used interchangeably to describe the commonly used process of compacting powders into tablets via conventional pharmaceutical tableting technology as well known in the art. One typical such process employs a rotary tablet machine, often referred to as a "press" or "compression machine", to compact the powders into tablets between upper and lower punches in a shaped die. This process produces a core having two opposed faces, formed by contact with an upper and lower punch, and having a belly band formed by contact with a die wall. Typically such compressed tablets will have at least one dimension of the major faces at least as long as the height of the belly band area between the major faces. Alternately, processes have been disclosed in the prior art to enable the "longitudinal compression" of tablet cores. When longitudinally compressed tablets are employed, it has been found that an aspect ratio (height between the major faces to width or diameter of the major faces) from about 1.5 to about 3.5, e.g., about 1.9 facilitates handling.

Tablets are typically compacted to a target weight and "hardness". Hardness is a term used in the art to describe the diametrical breaking strength as measured by conventional pharmaceutical hardness testing equipment, such as a Schleuniger Hardness Tester. In order to compare values across differently sized tablets, the breaking strength is normalized for the area of the break (which may be approximated as tablet diameter times thickness). This normalized value, expressed in kp/cm2, is sometimes referred in the art as "tablet tensile strength." A general discussion of tablet hardness testing is found in Leiberman et al., Pharmaceutical Dosage Forms—Tablets, Volume 2, 2nd ed., Marcel Dekker Inc., 1990, pp. 213-217, 327-329, which is incorporated by reference herein.

The medicaments manufactured according to the present invention, therefore, provide the desired shape, swallowability and appearance for a solid dosage form. Further, the dosage form of the invention provides improved onset of dissolution and disintegration, while not compromising swallowability of the dosage form. Use of the discontinuous coated regions in accordance with the invention permits the ability to add actives, colors, flavors, sensates and textures; impart improved swallowability, perception of speed, taste masking, and visual recognition to aid in product selection.

It will become apparent to those skilled in the art that various modifications to the preferred embodiments of the invention can be made by those skilled in the art without departing from the spirit or scope of the invention as defined by the appended claims.

EXAMPLES

Formula, Preparation Procedure and Viscosity for Polymers Employed to Prepare Discontinuous Coated Regioned Tablets Example 1: Preparation of Gelatin Solution

TABLE 1

| Formula(s) for Gelatin Solution: | | | | |
|---|---|---|---|---|
| | Formula A | | Formula B | |
| Material | Amount (g) | w/w (%) | Amount (g) | w/w (%) |
| Polysorbate 80 (Tween ® 80) | 4.0 | 0.9 | 4.0 | 1.1 |
| Purified water | 302.0 | 69.7 | 233.3 | 64.0 |
| Gelatin 220 Bloom (bone) | 94.0 | 21.7 | 94.0 | 25.8 |
| Color solution | 33.3 | 7.7 | 33.3 | 9.1 |
| TOTAL | 433.3 | 100.0 | 364.6 | 100.0 |

Preparation and Viscosity Testing Procedure:
1. Added polysorbate 80 and purified water to suitable glass bottle with screw cap. Mixed with magnetic stir bar until completely dissolved.
2. Added gelatin and allowed to rest at room temperature for 60 minutes to bloom.
3. Added color solution, stirred manually with metal spatula to distribute color, capped bottle, and placed in 55° C. oven overnight.
4. Determination of viscosity was performed with a Brookfield DV-II Pro using the small sample adapter and a suitable spindle:
   a. Water jacket temperature—55° C.
   b. Speed—30 rpm.

Example 2: Preparation of Hypromellose Solution

TABLE 2

| Formula for Hypromellose Solution: | | |
|---|---|---|
| | Formula C | |
| Material | Amount (g) | w/w (%) |
| Hypromellose(Pharmacoat ® 603[a]) | 90 | 25 |
| Purified water | 269 | 75 |
| TOTAL | 359 | 100 |

[a]Commercially available from Shin-Etsu Chemical

Preparation and Viscosity Testing Procedure:
1. Added hot purified water (80-90° C.) to suitable stainless steel pot with standard mixer and impeller.
2. Added Hypromellose (also known as hydropropylmethylcellulose, or HPMC) slowly and mixed with vortex until dispersed.
3. Set mixer to slowest speed, covered with foil, and mixed overnight. Solution was translucent the next day with no indication of foam.
4. Lower concentrations were prepared by dilution with purified water.
5. Determination of viscosity was performed with a Brookfield DV-II Pro using the small sample adapter and suitable spindles:
   a. Water jacket temperature—25° C.
   b. Speed—30 rpm.

Example 3: Preparation of Hydroxypropylcellulose (HPC) Solution

TABLE 3

| Formula for Hydroxypropylcellulose Solution: | | |
|---|---|---|
| | Formula D | |
| Material | Amount (g) | w/w (%) |
| Hydroxypropyl cellulose (Klucel ™ EXF[b]) | 60 | 16 |
| Purified water | 315 | 84 |
| TOTAL | 375 | 100 |

[b]Commercially available from Ashland Corporation

Preparation and Viscosity Testing Procedure:
1. Added hot purified water (80-90° C.) to suitable stainless steel pot with stand mixer and impeller.
2. Added HPC slowly and mixed with vortex until dispersed.
3. Set mixer to slowest speed, covered with foil, and mixed overnight. Solution was translucent the next day with no indication of foam.
4. Lower concentrations were prepared by dilution with purified water.

5. Determination of viscosity was performed with a Brookfield DV-II Pro using the small sample adapter and suitable spindles:
Water jacket temperature—25° C.
Speed—30 rpm.

The results of the viscosity testing for Examples 1-3 are set forth below and in FIG. 17.

TABLE 4

Viscosity

| Polymer | Concentration (%) | Viscosity (cP) | Spindle |
|---|---|---|---|
| Gelatin Solution | 21.7 | 159.9 | SC4-31 |
|  | 25.8 | 411.4 | SC4-31 |
| HPMC Solution | 5 | 8.30 | SC4-18 |
|  | 10 | 50.2 | SC4-18 |
|  | 13 | 119.0 | SC4-31 |
|  | 16 | 259.9 | SC4-31 |
|  | 20 | 999.8 | LV4 |
|  | 25 | 2559 | LV4 |
| HPC Solution | 6 | 53.9 | SC4-18 |
|  | 8 | 171.0 | SC4-31 |
|  | 9 | 254.9 | SC4-31 |
|  | 10 | 313.9 | SC4-31 |
|  | 12 | 765.8 | SC4-31 |
|  | 14 | 1620 | LV4 |
|  | 16 | 2499 | LV4 |

Example 5: Preparation of Tablet Core

TABLE 5

Formula for Placebo Tablet Core:

|  | Formula F | |
|---|---|---|
| Material | Amount (g) | w/w (%) |
| Lactose monohydrate (Fast Flo ® 316) | 2,587.0 | 49.75 |
| Microcrystalline cellulose (Avicel ® PH 102) | 2,587.0 | 49.75 |
| Magnesium stearate | 26.0 | 0.50 |
| TOTAL | 5,200.0 | 100 |

Procedure:
1. The magnesium stearate was passed through a 35 mesh screen with 10 grams of the microcrystalline cellulose.
2. The remaining microcrystalline cellulose was charged into a 16-qt. v-shell blender.
3. The magnesium stearate was layered and preblended on top of microcrystalline cellulose.
4. The lactose monohydrate was layered on top of magnesium stearate and preblended.
5. The mixture was blended for 5 minutes.
6. Tablets were compressed using a Natoli® NP-RD10 tablet press and Kinematics & Controls Corp. model 4400 vacuum powder filler through the following steps:
    a. 580 mg of blended material was dispensed into weigh boat with vacuum powder filler.
    b. Material was transferred from weigh boat to dye with custom dye extender attached.
    c. The tablet was compressed until upper punch contacted dye extender
        i. Target tablet weight—570 mg (accounting for material loss)
        ii. Target tablet length—0.6590" (16.7 mm).

Example 6: Preparation of Subcoat for Tablets

TABLE 6

Formula for Tablet Subcoat:

|  | Formula G | |
|---|---|---|
| Material | Amount (g) | w/w (%) |
| Hypromellose* (Methocel ® E5) | 138 | 8.21 |
| Castor oil (USP) | 0.562 | 0.03 |
| Purified water | 1,542 | 91.76 |
| TOTAL | 1,680.562 | 100.00 |

*Hypromellose: Also labeled hydroxypropylmethylcellulose

Procedure for Solution Preparation and Tablet Coating Using the Formula in Table 6.
1. Approximately half of the purified water was heated to 80-90° C. in a suitable vessel.
2. The hydroxypropylcellulose (hypromellose) was slowly added to the water with vortex.
3. The remaining room temperature water was added, followed by the castor oil.
4. The solution was covered with foil and continued mixing overnight on lowest speed.
5. 2.250 g of tablets was charged into O'Hara Labcoat 1 with 15" coating pan.
6. Sprayed 1.191 g of coating solution (4.6% weight gain):
    a. Nozzle—1.2 mm
    b. Aircap—2.7 mm
    c. Exhaust air—51.5° C.
    d. Air volume—150 cfm
    e. Pan speed—8.9 rpm
    f. Atomization air—20.3 psi
    g. Pattern air—26.2 psi
    h. Spray rate—15 g/min.

Example 7: Procedure for Application of Discontinuous Coated Regions

Part A: Application of Gelatin Discontinuous Coated Regions in Three Portions
Description of Discontinuous Coated Region Configuration:

The compressed and subcoated caplet cores from Example 6 were used to apply various discontinuous coated regions across the small axis. The gelatin solution from Example 1 (Table 1) was used. The discontinuous coated regions completely covered the section of the core utilizing a Qualicaps Bench-Top Capsule-Sealer (S-1). A single discontinuous coated region was applied across the center portion of the caplet, and two independent discontinuous coated regions were applied across the end caps, wherein the discontinuous coated region partially covered the angled portion of the end, and covered the round portion where the angle end meets the side body.

Part B: Procedure for Application of Discontinuous Coated Regions
1. The jacket of the gelatin pan is filled with heat transfer media (300 mL propylene glycol) and the heater is inserted into the base of the pan. The gelatin pan is then positioned on the pan base inside the system and the temperature sensor (thermocouple) is inserted into the port on the top of the pan.
2. The discontinuous coated regioning wheels are assembled and installed to apply the discontinuous coated region to a specified position on the caplet. The discontinuous coated region thickness, configuration, and location can be adjusted by using different wheels and spacer combinations. The doctor blades must also be selected and affixed in the correct locations, and the offset/lift-height must be set by adjusting the height of the deck plate using a knurled knob on the left side of the unit.
3. The system is powered on and the temperature controller is set to 57° C. The gelatin pan is manually raised into the "full up" position, activating the in-position switch causing the discontinuous coated regioning wheels to spin and the heater to activate. The gelatin pan is left in this position and the heat transfer media allowed to heat until reaching the set point temperature where it is maintained.
4. The gelatin pan is then manually lowered into the "down" position and gelatin is filled into the pan up to the fill mark. The gelatin pan is then returned to the "full up position", now partially submerging the bottom of the discontinuous coated regioning wheels in the gelatin solution (and reactivating the spinning of the discontinuous coated regioning wheels cartridge heater). The discontinuous coated regioning wheels are allowed to warm, spinning in the gelatin solutions, for 5 minutes prior to commencing discontinuous coated regioning.
5. The Caplets (from Example 6) are loaded into a carrier tray and placed in the start location on the top of the system. 'Start' is pressed on the front panel, and the carrier is carried, by means of a flight on a chain, along the carrier path, passing the contained caplets over the discontinuous coated regioning wheels which spin at 60 RPM counter to the movement direction of the carrier (while viewing the system from the front, the carrier moves from left to right, and the coating wheels spin counter-clockwise).
6. The carrier tray, containing the discontinuous coated regioned dosage forms, is set in a drying rack to dry for at least 1 hour.

Example 8: Addition of Discontinuous Coated Regions Providing Sweetener and Cooling The application procedure used in Example 7, Part B was utilized. 0.5 g of sucralose is added to the hypromellose solution in Example 2, and 0.1 g of yellow dye is added. In addition, 0.5 g of Cooler #2 (Serial Number 069450), commercially available from the International Flavors and Fragrances Corporation, is added to the HPC Solution in Example 3. In addition, 0.1 g of blue dye is added. Three solutions are then applied to the subcoated caplet cores from Example 6. The Hypromellose solution containing sucralose is applied to one end, the Gelatin solution from Example 1 is added to the center, and the HPC solution containing Cooler #2 is added to the third end. This sample provides for a release of three types of discontinuous coated regions, proving three benefits, including sweetness, ease of swallowability and a cooling sensate.

Example 9: Preparation of Melted Discontinuous Coated Region Material 200 g of Polyethylene glycol 8000 is heated to 80° C. and melted. An additional 4 g of Polyethylene Oxide WSR-301 (Molecular weight 4,000,000) is added and melted. 0.2 g of red colorant is added. The melted material mixture is applied in 3 separate discontinuous coated region structures and allowed to harden at room temperature. These three discontinuous coated regions add lubricity to a tablet upon hydration when swallowing, without the need to add excessive levels of coating material which may affect disintegration of the dosage form. The procedure in Example 7 is utilized, except the temperature controller is set to 70° C.

In accordance with the present invention, discontinuous coated regions having various configurations are used to provide benefits to pharmaceutical dosage forms. The discontinuous coated regions provide the ability to vary the types of materials used in the dosage form. In addition, discontinuous coated regions are proposed for use on compressed caplets or tablets. In one embodiment a compressed tablet is coated (or sub-coated) prior to the application of the discontinuous coated region; which may improve ease of swallowing or adherence of the discontinuous coated region.

Embodiment 1: Flavorings and Sensates in Tablet Discontinuous Coated Regions

In this embodiment the discontinuous coated regions which are added to the surface of the caplet contain at least one flavoring or sensate. The sensate may contain a cooling material, a warming material or an alternative sensate. In one version of this embodiment the dosage form has multiple discontinuous coated regions; for example one discontinuous coated region which contains a sweetener, one discontinuous coated region which contains a warming sensate and one discontinuous coated region which contains a cooling sensate. In another version of this embodiment, the discontinuous coated region contains an acidulant such as citric acid, malic acid or fumaric acid. In another version of this embodiment, one discontinuous coated region contains sodium bicarbonate and another discontinuous coated region contains citric acid; creating a combined acid couple ("fizzing action") upon swallowing. In one embodiment, the caplet contains a subcoat which contains one flavoring material or sensate and the discontinuous coated region contains a separate flavor, projecting sequential flavoring experience upon ingestion.

Embodiment 2: Swallowability Improvements Through Use of Tablet Discontinuous Coated Regions In this embodiment the discontinuous coated regions incorporate a material which helps to aid in the swallowability, making the form easier to swallow. This may be through the use of a quickly hydrating polymer. Alternatively, it may be through the addition of a salivation inducing agent such as an acid or succulence sensate.

Embodiment 3: Angled, Spiralled, or Patterned Tablet Discontinuous Coated Regions In this embodiment the discontinuous coated region is applied as at an angle or in a spiraled pattern. This can help to convey an elegant look or ease of swallowing as the discontinuous coated region is more uniformly covering the caplet. In order to apply the discontinuous coated region across the circular width of the form, the discontinuous coated region may need to be tapered at the top and bottom. In another version of this embodiment the discontinuous coated region itself is patterned or labelled with product information such as brand, indicia or dose.

Embodiment 4: Speed Perception Through Rapidly Dissolving Discontinuous Coated Regions and Material Selection In this embodiment, the speed of dissolution is conveyed through the addition of a fast dissolving discontinuous coated region or a discontinuous coated region which comprises openings. Fast dissolving materials may include polymers which disintegrate quickly such as pullulan, starch or HPMC. Openings may show the core underneath the discontinuous coated region. Optionally, the discontinuous coated region may include printed portions which convey speed or depth (such as 3D cone shapes).

Embodiment 5: Addition of Active Ingredients to Discontinuous Coated Region

In this embodiment an active ingredient is added to the discontinuous coated region. In one version a higher dose active ingredient such as acetaminophen or ibuprofen is contained in the compressed core tablet and a second low dose active ingredient (such as cetirizine or diphenhydramine) is contained in the discontinuous coated region portion.

The foregoing examples are not intended to limit the scope of the present invention, which may be set out in the claims. In particular, various equivalents and substitutions will be recognized by those skilled in the art in view of the foregoing disclosure and these are contemplated to be within the scope of the invention.

What is claimed is:

1. A method of making a dosage form suitable for ingestion by a human, comprising:
   (a) preparing a tablet- or caplet-shaped substrate; and
   (b) positioning at least two discontinuous coated regions on a surface of the tablet- or caplet-shaped substrate, wherein the at least two discontinuous coated regions contain at least one flavoring or sensate, and wherein each of the at least two discontinuous coated regions contain a separate flavoring or sensate.

2. The method of claim 1, wherein the at least two discontinuous coated regions are extrusion coated on the tablet- or caplet-shaped substrate.

3. The method of claim 1, wherein the at least two discontinuous coated regions are screen coated on the tablet- or caplet-shaped substrate.

4. The method of claim 1, wherein the at least two discontinuous coated regions are printed on the tablet- or caplet-shaped substrate.

5. The method of claim 1, wherein the at least two discontinuous coated regions are brush coated on the tablet- or caplet-shaped substrate.

6. The method of claim 1, wherein the at least two discontinuous coated regions are sprayed on the tablet- or caplet-shaped substrate.

7. The method of claim 1, wherein the at least two discontinuous coated regions are painted on the tablet- or caplet-shaped substrate.

8. The method of claim 1, wherein the at least two discontinuous coated regions are 3D printed on the tablet- or caplet-shaped substrate.

9. The method of claim 1, wherein the at least two discontinuous coated regions comprise a material selected from the group consisting of polymers, meltable carbohydrates, fats, fatty acid esters, phospholipids, waxes, and gelling material,
   wherein the fats are selected from the group consisting of hydrogenated vegetable oils selected from cocoa butter, hydrogenated palm kernel oil, hydrogenated cottonseed oil, hydrogenated sunflower oil, and hydrogenated soybean oil; and free fatty acids and their salts,
   wherein the fatty acid esters are selected from the group consisting of sucrose fatty acid esters, mono, di, and triglycerides, glyceryl behenate, glyceryl palmitostearate, glyceryl monostearate, glyceryl tristearate, glyceryl trilaurylate, glyceryl myristate, glycowax, lauroyl macrogol-32 glycerides, and stearoyl macrogol-32 glycerides,
   wherein the phospholipids are selected from the group consisting of phosphotidyl choline, phosphotidyl serine, phosphotidyl enositol, and phosphotidic acid,
   wherein the waxes are selected from the group consisting of carnauba wax, spermaceti wax, beeswax, candelilla wax, shellac wax, microcrystalline wax, and paraffin wax,
   wherein the polymers are selected from the group consisting of polyethylene oxide, polyvinyl acetate and polycapralactone; and water soluble film forming polymers selected from hydroxypropyl cellulose, hypromellose, methylcellulose, pullulan, modified starches, and hydroxyethylcellulose,
   wherein the carbohydrate is selected from the group consisting of polysaccharides selected from polyfructose, polydextrose, inulin, hydrogen starch hydrolysate; isomalt; and sugar alcohols selected from as xylitol, sorbitol erythritol and mixtures thereof, and
   wherein the gelling material is selected from the group consisting of gelatin, pectin, gellan gum, carrageenan, and xanthan gum.

* * * * *